(12) United States Patent
Ahn et al.

(10) Patent No.: US 12,103,945 B2
(45) Date of Patent: Oct. 1, 2024

(54) CRYSTALLINE FORM OF VASCULAR LEAKAGE BLOCKER COMPOUND

(71) Applicant: Curacle Co., Ltd., Seoul (KR)

(72) Inventors: Koo Hyeon Ahn, Seongnam-si (KR); Myung-Hwa Kim, Seongnam-si (KR); Jung-In Pyo, Seongnam-si (KR); Chul Su Baek, Seongnam-si (KR); Sung Hwan Kim, Seongnam-si (KR)

(73) Assignee: CURACLE CO., LTD., Seoul (KR)

( * ) Notice: Subject to any disclaimer, the term of this patent is extended or adjusted under 35 U.S.C. 154(b) by 649 days.

(21) Appl. No.: 17/421,165

(22) PCT Filed: Oct. 5, 2020

(86) PCT No.: PCT/KR2020/013505
§ 371 (c)(1),
(2) Date: Jul. 7, 2021

(87) PCT Pub. No.: WO2021/225233
PCT Pub. Date: Nov. 11, 2021

(65) Prior Publication Data
US 2022/0259256 A1    Aug. 18, 2022

(30) Foreign Application Priority Data
May 4, 2020 (KR) .................. 10-2020-0053232

(51) Int. Cl.
*C07J 17/00* (2006.01)

(52) U.S. Cl.
CPC ......... *C07J 17/005* (2013.01); *C07B 2200/13* (2013.01)

(58) Field of Classification Search
CPC .. C07B 2200/13; A61K 31/58; A61K 31/704; C07J 9/005
See application file for complete search history.

(56) References Cited

U.S. PATENT DOCUMENTS

| 2012/0245110 A1* | 9/2012 | Kwon | A61P 17/02 540/113 |
| 2015/0057440 A1* | 2/2015 | Ren | A61P 35/00 536/5 |

FOREIGN PATENT DOCUMENTS

| KR | 1020110047170 A | 5/2011 |
| KR | 1014817090 B1 | 2/2015 |
| KR | 102124470 B1 | 6/2020 |

OTHER PUBLICATIONS

Byrn et al., "Pharmaceutical Solids: A Strategic Approach to Regulatory Considerations", Pharma. Res., 12(7), pp. 945-954, 1995, 11 pgs.
Hilfiker et al., "Polymorphism in the Pharmaceutical Industry", Wile-VCH, 2006, 425 pgs.
Stahly,P.,Salt selection of pharmaceutical products, Importance of screening for polymorphs of crystals, Pharmaceutics, 2006, vol. 66, No. 6, p. 435-439, with partial English machine translation, 6 pgs.
Rossi et al., "Approaches for multi-gram scale isolation of enantiomers for drug discovery", Expert Opinion on Drug Discovery, 12(12), pp. 1253-1269, 2017, 18 pgs.
Zhang, H. et al., "Sac-1004, a vascular leakage blocker, reduces cerebral ishemia-reprefusion injury by suppressing blook-brain barrier disruption and inflammation," Journal of Neuroinflammation (2017) 14:122, 16 pgs.
Batbold, D. et al., "Sac-1004, a pseudo-sugar derivative of cholesterol, restores erectile function through reconstruction of nonleaky and functional cavernous angiogenesis in the streptozotocin induced diabetic mouse," Journal of Urology (2016) 195:6, pp. 1936-1946.
Maharjan, S. et al., "Sac-1004, a novel vascular leakage blocker, enhances endothelial barrier through the CAMP/Rac/cortactin pathway," Biochemical and Biophysical Research Communications 435 (2013), pp. 420-427.
Caira M.R., 'Crystalline Polymorphism of Organic Compounds', Design of Organic solids, Weber E et al."ED", Springer, 1998, 46 pgs.
Balbach, S. et al., Pharmaceutical Evaluation of Early Development Candidates "The 100 mg approach", International Journal of Pharmaceutics, 2004, vol. 275, pp. 1-12.
Singhal, D. et al., 'Drug polymorphism and dosage form design: a practical perspective', Advanced Drug Delivery Reviews, 2004, vol. 56, pp. 335-347.
Morissette, Sherry L.et al., "High-throughput crystallization: polymorphs, salts, co-crystals and solvates of pharmaceutical solids", Advanced Drug Delivery Reviews, 2004, v.56, pp. 275-300.
Variankayal, Narayan, et al., "From Form to Function: Crystallization of Active Pharmaceutical Ingredients", AIChE Journal, Jul. 2008, vol. 54(7), pp. 1682-1688.
Hilfker et al., "Relevance of Solid-State Properties for Pharmaceutical Products", Polymorphism: in the Pharmaceutical Industry, 2006, pp. 1-19.
Braga et al., "Crystal Polymorphism and Multiple Crystal Forms", Springer-Verlag Berlin Heidelberg, Published Feb. 25, 2009, pp. 27.

* cited by examiner

*Primary Examiner* — Pancham Bakshi
(74) *Attorney, Agent, or Firm* — Fredrikson & Byron, P.A.

(57) ABSTRACT

The present invention relates to a crystalline form of (E)-methyl 6-((3S,8S,9S,10R,13S,14S,17R)-3-(((5S,6R)-5-acetoxy-6-(acetoxytnethyl)-5,6-dihydro-2H-pyran-2-yl)oxy)-10,13-dimethyl-2,3,4,7,8,9,10.11,12,13,14,15,16,17-tetradecahydro-1H-cyclopenta[a]phenanthrene-17-yl)hept-5-enoate and a blood vessel leak blocker comprising the same. The novel crystalline form has high purity, excellent stability, excellent long-term storage and pharmaceutical stability, and can be used as a vascular leakage blocker, so it is very advantageous in producing high-quality drug substances.

5 Claims, 14 Drawing Sheets

CRYSTALLINE FORM OF VASCULAR LEAKAGE BLOCKER COMPOUND

RELATED APPLICATIONS

This application is a 35 U.S.C. 371 national stage filing from International Application No. PCT/KR2020/013505, filed Oct. 5, 2020, which claims priority to Korean Application No. 10-2020-0053232, filed May 4, 2020, the teachings of which are incorporated herein by reference.

CROSS-REFERENCES TO RELATED APPLICATION

This patent application claims the benefit of priority from Korean Patent Application No. 10-2020-0053232, filed on May 4, 2020, the contents of which are incorporated herein by reference.

TECHNICAL FIELD

The present invention relates to a novel crystalline form of a vascular leakage blocker compound.

BACKGROUND ART

The compound represented by formula 1 has the compound name (E)-methyl 6-((3S,8S,9S,10R,13S,14S,17R)-3-(((5S,6R)-5-acetoxy-6-(acetoxyraethyl)-5,6-dihydro-2H-pyran-2-yl)oxy)-10,13-dimethyl-2,3,4,7,8,9,10,11,12,13,14,15,16,17-tetradecahydro-1H-cyclopenta[a]phenanthrene-17-yl)hept-5-enoate, and is a compound disclosed in Korean Patent Laid-Open Publication No. 10-2011-0047170 under the code name SAC-1004.

[Formula 1]

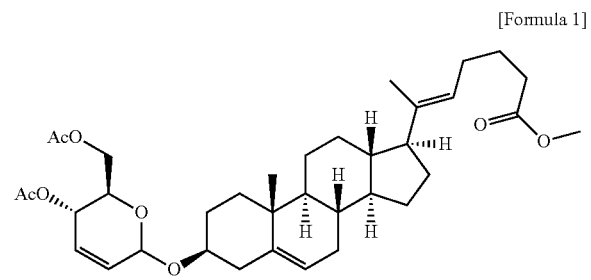

The compound inhibits the death of vascular endothelial cells, suppresses the formation of actin stress fibers induced by VEGF, increases the structure of cortical act in ring, and improves the stability of TJ (tight junction) between vascular cells, thereby inhibiting vascular leakage. The compound not only inhibits the permeability of blood vessels, but also has excellent activity to restore the integrity of damaged blood vessels. Therefore, it is known that the compound can be effectively used for preventing or treating various diseases caused by vascular leakage.

Koren Patent Application No. 10-2019-0166864 discloses a new chemical preparation method capable of separating and mass-producing stereoisomers of the compound of formula 1, and preparing the compound in high yield.

On the other hand, polymorphs refer to crystalline solids that have the same molecular structure, but whose crystal structure is changed by alterations in packing and molecular conformation of crystals.

The criterion for selecting a good crystalline form is due to the most, important physicochemical properties required by drugs. The selection of the optimized crystalline form can vary depending on the purpose, such as choosing the thermodynamically most stable one, choosing the one optimized for the production of pharmaceutical raw materials and finished products, improving the solubility and dissolution rate of drugs, or changing pharmacokinetic properties.

Accordingly, the present inventors disclose the first crystalline form of (E)-methyl 6-((3S,8S, 9S, 10R, 13S, 14S, 17R)-3-(((5S,6R)-5-acetoxy-6-(aeetoxymethyl)-5,6-dihydro-2H-pyran-2-yl)oxy)-10,13-dimethyl-2,3,4,7,8,9,10,11,12,13,14,15,16,17-tetradecahydro-1H-cyclopenta[a]phenanthrene-17-yl)hept-5-enoate, the preparation method therefor, and the physicochemical properties of the novel crystalline form.

DISCLOSURE

Technical Problem

It is an object of the present invention to provide a novel crystalline form of the compound (E)-methyl 6-((3S,8S,9S,10R,13S,14S,17R)-3-(((5S,6R)-5-acetoxy-6-(acetoxymethyl)-5,6-dihydro-2H-pyran-2-yl)oxy)-10,13-dimethyl-2,3,4.7.8,9,10,11,12,13,14,15,16,17-tetradecahydro-1H-cyclopenta[a]phenanthrene-17-yl)hept-5-enoate.

It is another object of the present invention to provide a vascular leakage blocker comprising a novel crystalline form of the compound.

Technical Solution

To achieve the above objects, in one aspect of the present invention, the present invention provides a compound characterized in that the proportion of α-isomer of the compound represented by (E)-methyl 6-((3S,8S,9S,10R,13S,14S,17R)-3-(((5S,6R)-5-acetoxy-6-(acetoxymethyl)-5,6-dihydro-2H-pyran-2-yl)oxy)-2,3,4,7,8,9,10,11,12,13,14,15,10,17-tetradecahydro-1H-cyclopenta[a]phenanthrene-17-yl)hept-5-enoate is 85% or more and is in a solid state.

In another aspect of the present invention, the present invention provides a compound represented by (E)-methyl 6-((3S,8S,9S,10R,13S,14S,17R)-3-(((2S,5S,6R)-5-acetoxy-6-(acetoxymethyl)-5,6-dihydro-2H-pyran-2-yl)oxy)-10,13-dimethyl-2,3,4,7,8,9,10,11,12,13,14,15,16,17-tetradecahydro-1H-cyclopenta[a]phenanthrene-17-yl)hept-5-enoate.

In one aspect of the present invention, the present invention provides a crystalline form I of (B)-methyl 6-((3S,8S,9S,10R,13S,14S,17R)-3-(((5S,6R)-5-acetoxy-6-(acetoxymethyl)-5,6-dihydro-2H-pyran-2-yl)oxy)-10,13-dimethyl-2,3,4,7,8,9,10,11,12,13,14,15,16,17-tetradecahydro-1H-cyclopenta[a]phenanthrene-17-yl)hept-5-enoate having peaks at the following 2θ diffraction angles in the X-ray powder diffraction pattern:
16.0°±0.2°, 19.5°±0.2°, 18.3°±0.2°, 15.1°±0.2°, 21.9°±0.2°.

In another aspect of the present invention, the present invention provides a crystalline form H of (E)-methyl 6-((3S,8S, 9S, 10R, 13S, 14S, 17R)-3-(((5S,6R)-5-acetoxy-6-(acetoxymethyl)-5,6-dihydro-2H-pyran-2-yl)oxy)-10,13-dimethyl-2.3,4,7,8,9,10,11,12,13,14,15,16,17-tetradecahydro-1H-cyclopenta[a]phenanthrene-17-yl)hept-5-enoate having peaks at the following 29 diffraction angles in the X-ray powder diffraction pattern:
17.3°±0.2°, 11.4°±0.2°, 35.2°±0.2°, 19.0°±0.2°, 15.3°±0.2°, 5.7°±0.2°.

In another aspect of the present invention, the present invention provides a crystalline form III of (E)-methyl 6-((3S,8S,9S,10R,13S,14S,17R)-3-(((5S,6R)-5-acetoxy-6-(acetoxymethyl)-5,6-dihydro-2H-pyran-2-yl)oxy)-10,13-dimethyl-2,3,4,7,8,9,10,11,12,13,14,15.16,17-tetradecahydro-1H-cyclopenta[a]phenanthrene-17-yl)hept-5-enoate having peaks at the following 2θ diffraction angles in the X-ray powder diffraction pattern:

15.6°±0.2°, 18.2°±0.2°, 14.4°±0.2°, 24.6°±0.2°, 16.9°±0.2°, 17.2°±0.2°.

In another aspect of the present invention, the present invention provides a crystalline form IV of (E)-methyl 6-((3S,8S,9S,10R,13S,14S,17R)-3-(((5S,6R)-5-acetoxy-6-(acetoxymethyl)-5,6-dihydro-2H-pyran-2-yl)oxy)-10,13-dimethyl-2,3,4,7,8,9,10,11,12,13,14,15,16,17-tetradecahydro-1H-cyclopenta[a]phenanthrene-17-yl)hept-5-enoate having peaks at the following 2θ diffraction angles in the X-ray powder diffraction pattern:

15.3°±0.2°, 22.4°±0.2°, 17.2°±0.2°, 36.5°±0.2°, 24.8°±0.2°, 22.7°±0.2°, 11.7°±0.2°, 18.5°±0.2°, 21.8°±0.2°, 23.8°±0.2°, 16.3°±0.2°, 17.6°±0.2°.

In another aspect of the present invention, the present invention provides a crystalline form V of (B)-methyl 6-((3S,8S, 9S, 10R, 13S, 14S, 17R)-3-(((5S,6R)-5-acetoxy-6-(acetoxymethyl)-5,6-dihydro-2H-pyran-2-yl)oxy)-10,13-dimethyl-2,3,4,7,8,9,10,11,12,13,14,15,16,17-tetradecahydro-1H-cyclopenta[a]phenanthrene-17-yl)hept-5-enoate having peaks at the following 2θ diffraction angles in the X-ray powder diffraction pattern:

23.8°±0.2°, 16.2°±0.2°, 17.4°±0.2°, 35.3°±0.2°, 26.2°±0.2°, 36.6°±0.2°, 22.2°±0.2°, 20.7°±0.2°.

In another aspect of the present invention, the present invention provides a pharmaceutical composition for preventing or treating vascular leakage disease comprising any one of the compounds and the novel crystalline forms I to V of (E)-methyl 6-((3S,8S, 9S, 10R, 13S, 14S, 17R)-3-(((5S, 6R)-5-acetoxy-6-(acetoxymethyl)-5,6-dihydro-2H-pyran-2-yl) oxy)-10,13-dimethyl-2,3,4,7,8,9,10,11,12,13,14,15,16,17-tetradecahydro-1H-cycloponta[a]phenanthren(c)-17-yl) hept-5-enoate.

Advantageous Effect

The present invention provides a novel crystalline form of (S)-methyl 6-((3S,8S,9S,10R,13S,14S,17R)-3-(((5S,6R)-5-acetoxy-6-(acetoxymethyl)-S, 6-dihydro-2H-pyran-2-yl) oxy)-10,13-dimethyl-2,3,4,7,8,9,10,11,12,13,14,15,16,17-tetradecahydro-1H-cyclopenta[a]phenanthrene-17-yl-hept-5-enoate, the compound represented by formula 1, and a preparation method thereof. The novel crystalline form has high purity, excellent stability, excellent long-term storage and pharmaceutical stability, and can be used as a vascular leakage blocker, so it is very advantageous in producing high-quality drug substances.

BEST MODE

Figure 1A:
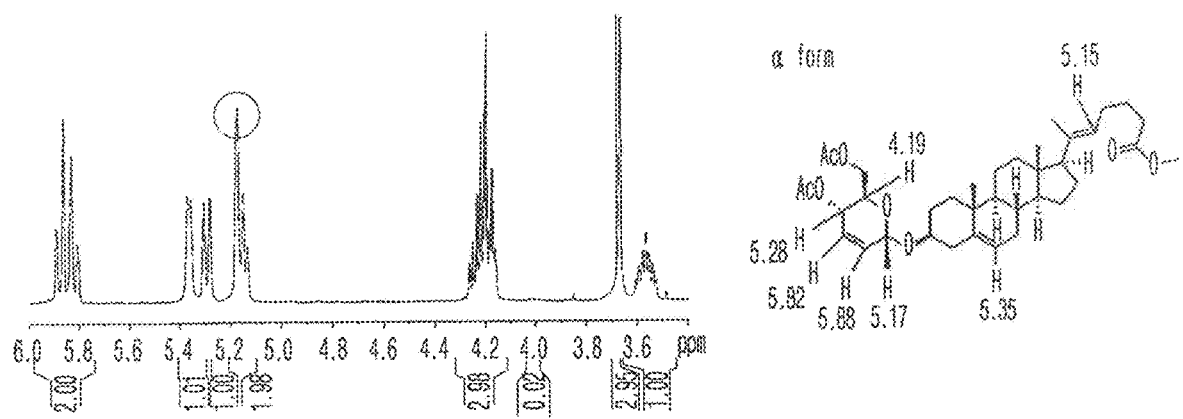
FIG. 1A is a diagram showing the results of NMR analysis to confirm the structures of α-isomer of the compound 1 prepared in Preparative Example 1, and the stereochemical structures of the α-isomer.

Hereinafter, the present invention is described in detail.

The embodiments of this invention can be modified in various other forms, and the scope of the present invention is not limited to the embodiments described below. It is well understood by those in the art who has the average knowledge on this field that the embodiments of the present invention are given to explain the present invention more precisely. In addition, the "inclusion" of an element throughout the specification does not exclude other elements, but may include other elements, unless specifically stated otherwise.

[Formula 1]

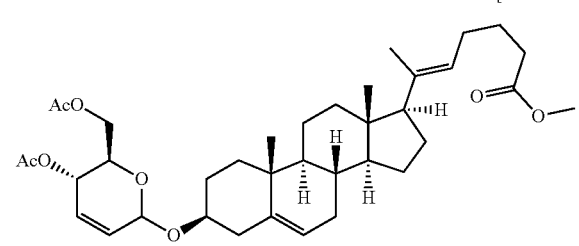

(E)-methyl 6-((3S,8S,9S,10R,13S,14S,17R)-3-H(5S,6R)-5-acetoxy-6-(acetoxymethyl)-5,6-dihydro-2H-pyran-2-yl)oxy)-10,13-dimethyl-2,3,4,7,8,9,10,11,12,13,14,15,16,17-tetradecahydro-1H-cyclopenta[a]phenanthrene-17-yl)hept-5-enoate At this time, among the two stereochemical structures of the compound of formula 1, a structure showing a crystalline form is (E)-methyl 6-((3S,8S,9S,10R,13S,14S,17R)-3-(((2S,5S,6R)-5-acetoxy-6-(acetoxymethyl)-5,6-dihydro-2H-pyran-2-yl)oxy)-10,13-dimethyl-2,3,4,7,8,9,10,11,12,13,14,15,16,17-tetradecahydro-1H-cyclopenta[a]phenanthrene-17-yl)hept-5-enoate. In one aspect of the present invention, the present invention provides a compound characterized in that the ratio of α-isomer of the compound represented by (E)-methyl 6-((3S,8S,9S,10R,13S,14S,17R)-3-(((5S,6R)-5-acetoxy-6-(acetoxymethyl)-5,6-dihydro-2H-pyran-2-yl)oxy)-10,13-dimethyl-2,3,4,7,8,9,10,11,12,13,14,15,16,17-tetradecahydro-1H-cyclopenta[a]phenanthrene-17-yl)hept-5-enoate is 85% or more and is in a solid state.

At this time, the ratio of the αisomer can be 87% or more, 89% or more, 90% or more, 92% or more, 95% or more, 98% or more, or 99% or more.

In another aspect of the present invention, the present invention provides a compound represented by (E)-methyl 6-((35,8S,9S,10R,13S,14S,17R)-3-(((2S,5S,6R)-5-acetoxy-6-(acetoxymethyl)-5,6-dihydro-2H-pyran-2-yl)oxy)-10,13-dimethyl-2,3,4,7,8,9,10,11,12,13,14,15,16,17-tetradecahydro-1H-cyclopenta[a]phenanthrene-17-yl)hept-5-enoate.

In another aspect of the present invention, the present invention provides a novel crystalline form I of the compound represented by (E)-methyl 6-((3S,8S,9S,10R,13S,14S,17R)-3-(((2S,5S,6R)-5-acetoxy-6-(acetoxymethyl)-5,6-dihydro-2H-pyran-2-yl)oxy)-10,13-dimethyl-2,3,4,7,8,9,20,11,12.13,14,15,16,17-tetradecahydro-1H-cyclopenta[a]phenanthrene-17-yl) hept-5-enoate having the peaks with 2θ diffraction angles of 16.0°±0.2°, 19.5°±0.2°, 18.3°±0.2°, 15.1°±0.2°, and 21.9°±0.2° in X-ray powder diffraction pattern (XRPD).

At this time, the crystalline form I can further include the peaks with 2θ diffraction angles of 10.7°±0.2°, 8.9°±0.2°, 17.8°±0.2°, 21.3°±0.2°, and 17.0°±0.2°.

In addition, the crystalline form I can further include the peaks with 2θ diffraction angles of 14.1°±0.2°, 20.5°±0.2°, and 11.7°±0.2°.

Further, the crystalline form I can include the peaks with 2θ diffraction angles of 24.0°±0.2°, 24.6°±0.2°, and 26.1°35 0.2°. Or, the crystalline form I can further include the peaks with 2θ diffraction angles of 24.0°±0.2°, 24.6°±0.2°, and 26.1°±0.2°.

For example, the crystalline form I can be a crystalline form having the characteristic peaks with 2θ diffraction angles of 8.9°±0.2°, 10.7°±0.2°, 11.7°±0.2°, 14.1°±0.2°, 15.1°±0.2°, 16.0°±0.2°, 17.2°±0.2°, 17.8°±0.2°, 18.3°±0.2°, 19.5°±0.2°, 20.5°±0.2°, 21.3°±0.2°, 21.9°±0.2°, 24.0°±0.2°, 24.6°±0.2°, and 26.1°±0.2° having a relative intensity (I/I$_0$) of 10% or more.

In addition, the present invention provides a novel crystalline form that exhibits an endothermic peak of 100.96° C.±3° C. in differential scanning calorimetry (DSC).

In one aspect of the present invention, the present invention provides a novel crystalline form II of the compound represented by (E)-methyl 6-((3S,8S,9S,10R,13S,14S,17R)-3-(((25,5S,6R)-5-acetoxy-6-(acetoxymethyl)-5,6-dihydro-2H-pyran-2-yl)oxy)-10,13-dimethyl-2,3,4,7,8,9,10,11,12,13,14,15,16,17-tetradecahydro-1H-cyclopental[a]phenanthrene-17-yl)hept-5-enoate having the peaks with 2θ diffraction angles of 17.3°±0.2°, 11.4°±0.2°, 35.2°±0.2°, 19.0°±0.2°, 15.3°±0.2°, and 5.7°±0.2° in X-ray powder diffraction pattern (XRPD).

In one aspect of the present invention, the present invention provides a novel crystalline form III of the compound represented by (E)-methyl 6-((3S,8S,9S,10R,13S,14S,17R)-3-(((2S,5S,6R)-5-acetoxy-6-(acetoxymethyl)-5,6-dihydro-2H-pyran-2-yl)oxy)-10,13-dimethyl-2,3,4,7,8,9,10,11,12,13,14,15,16,17-tetradecahydro-1H-cyclopenta[a]phenanthrene-17-yl)hept-5-enoate having the peaks with 2θ diffraction angles of 15.6°±0.2°, 18.2°±0.2°, 14.4°±0.2°, 24.6°±0.2°, 16.9°±0.2°, and 17.2°±0.2° in X-ray powder diffraction pattern (XRPD).

At this time, the crystalline form III can further include the peaks with 2θ diffraction angles of 8.5°±0.2°, 24.3°±0.2°, 15.0°±0.2°, 3.5°±0.2°, 9.3°±0.2°, 20.6°±0.2°, 9.0°±0.2°, 24.0°±0.2°, 20.9°±0.2°, and 20.7°±0.2°.

For example, the crystalline form III can be a crystalline form having the characteristic peaks with 2θ diffraction angles of 3.5°±0.2°, 8.5°±0.2°, 9.0°±0.2°, 9.3°±0.2°, 14.4°±0.2°, 15.0°±0.2°, 15.6°±0.2°, 16.9°±0.2°, 17.2°±0.2°, 18.2°±0.2°, 20.6°±0.2°, 20.7°±0.2°, 20.9°±0.2°, 24.0°±0.2°, 24.3°±0.2°, and 24.6°±0.2° having a relative intensity (I/I$_0$) of 10% or more.

In one aspect of the present invention, the present invention provides a novel crystalline form IV of the compound represented by (E)-methyl 6-((3S,8S,9S,10R,13S,14S,17R)-3-(2S,5S,6R)-5-acetoxy-6-(acetoxymethyl)-5,6-dihydro-2H-pyran-2-yl)oxy)-10,13-dimethyl-2,3,4,7,8,9,10,11,12,13,14,15,16,17-tetradecahydro-1H-cyclopenta[a]phenanthrene-17-yl)hept-5-enoate having the peaks with 2θ diffraction angles of 15.3°±0.2°, 22.4°±0.2°, 17.2°±0.2°, 36.5°±0.2°, 24.8°±0.2°, 22.7°±0.2°, 11.7°±0.2°, 18.5°±0.2°, 21.8°±0.2°, 23.8°±0.2°, 16.3°±0.2°, and 17.6°±0.2° in X-ray powder diffraction pattern (XRPD).

At this time, the crystalline form IV can further include the peaks with 2θ diffraction angles of 26.5°±0.2°, 19.6°±0.2°, 19.1°±0.2°, 16.6°±0.2°, 23.4°±0.2°, 11.5°±0.2°, 18.8°±0.2°, 35.2°±0.2°, 15.6°±0.2°, 18.0°±0.2°, 20.1°±0.2°, 34.7°±0.2°, 47.1°±0.2°, 10.8°±0.2°, 5.9°±0.2°, and 14.3°±0.2°.

For example, the crystalline form IV can be a crystalline form having the characteristic peaks with 2θ diffraction angles of 5.9°±0.2°, 10.8°±0.2°, 11.5°±0.2°, 11.7°±0.2°, 14.3°±0.2°, 15.3°±0.2°, 15.6°±0.2°, 16.3°±0.2°, 16.6°±0.2°, 17.2°±0.2°, 17.6°±0.2°, 18.0°±0.2°, 18.5°±0.2°, 18.8°±0.2°, 19.1°±0.2°, 19.6°±0.2°, 20.1°±0.2°, 21.8°±0.2°, 22.4°±0.2°, 22.7°±0.2°, 23.4°±0.2°, 23.8°±0.2°, 24.8°±0.2°, 26.5°±0.2°, 34.7°±0.2°, 35.2°±0.2°, 36.5°±0.2°, and 47.1°±0.2° having a relative intensity (I/I$_0$) of 10% or more.

In one aspect of the present invention, the present invention provides a novel crystalline form V of the compound represented by (E)-methyl 6-((3S,8S,9S,10R,13S,14S,17R)-3-(((2S,5S,6R)-5-acetoxy-6-(acetoxymethyl)-5,6-dihydro-2H-pyran-2-yl)oxy)-10,13-dimethyl-2,3,4,7,8,9,10,11,12,13,14,15,16,17-tetradecahydro-1H-cyclopenta[a]phenanthrene-17-yl)hept-5-enoate having the peaks with 2θ diffraction angles of 23.8°±0.2°, 16.2°±0.2°, 17.4°±0.2°, 35.3°±0.2°, 26.0°±0.2°, 36.6°±0.2°, 22.2°±0.2°, and 20.7°±0.2° in X-ray powder diffraction pattern (XRPD).

At this time, the crystalline form V can further include the peaks with 2θ diffraction angles of 17.7°±0.2°, 18.6°±0.2°, 11.5°±0.2°, 15.1°±0.2°, 15.4°±0.2°, 19.0°±0.2°, 19.4°±0.2°, 21.8°±0.2°, 21.6°±0.2°, 22.9°±0.2°, 36.0°±0.2°, 30.1°±0.2°, 18.4°±0.2°, 23.3°±0.2°, 37.5°±0.2°, and 11.8°±0.2°.

For example, the crystalline form V can be a crystalline form having the characteristic peaks with 2θ diffraction angles of 11.5°±0.2°, 11.8°±0.2°, 15.1°±0.2°, 15.4°±0.2°, 16.2°±0.2°, 17.4°±0.2°, 17.7°±0.2°, 18.4°±0.2°, 18.6°±0.2°, 19.0°±0.2°, 19.4°±0.2°, 20.7°±0.2°, 21.6°±0.2°, 21.8°±0.2°, 22.2°±0.2°, 22.9°±0.2°, 23.3°±0.2°, 23.8°±0.2°, 26.0°±0.2°, 30.1°±0.2°, 35.3°±0.2°, 36.0°±0.2°, 36.6°±0.2°, and 37.5°±0.2° having a relative intensity (I/I$_0$) of 10% or more.

In one aspect of the present invention, the present invention provides a novel crystalline form VI of the compound represented by (E)-methyl 6-((3S,8S,9S,10R,13S,14S,17R)-3-(((2S,5S,6R)-5-acetoxy-6-(acetoxymethyl)-5,6-dihydro-2H-pyran-2-yl)oxy)-10,13-dimethyl-2,3,4,7,8,9,10,11,12,13,14,15,16,17-tetradecahydro-1H-cyclopenta[a]phenanthrene-17-yl)hept-5-enoate having the peaks with 2θ diffraction angles of 17.3°±0.2°, 15.2°±0.2°, and 11.5°±0.2° in X-ray powder diffraction pattern (XRPD).

At this time, the crystalline form VI can further include the peaks with 2θ diffraction angles of 16.2°±0.2°, 21.6°±0.2°, 36.1°±0.2°, 23.2°±0.2°, 19.6°±0.2°, 22.0°±0.2°, 17.6°±0.2°, and 18.5°±0.2°.

For example, the crystalline form VI can be a crystalline form having the characteristic peaks with 2θ diffraction angles of 11.5°±0.2°, 15.2°±0.2°, 16.2°±0.2°, 17.3°±0.2°, 17.6°±0.2°, 18.5°±0.2°, 19.6°±0.2°, 21.6°±0.2, 22.0°±0.2°, 23.2°±0.2°, and 36.1°±0.2° having a relative intensity (I/I$_0$) of 10% or more.

In one aspect of the present invention, the present invention provides a novel crystalline form VII of the compound represented by (E)-methyl 6-((3S,8S,9S,10R,13S,14S,17R)-3-(((2S,5S,6R)-5-acetoxy-6-(acetoxymethyl)-5,6-dihydro-2H-pyran-2-yl)oxy)-10,13-dimethyl-2,3,4,7,8,9,10,11,12,13,14,15,16,17-tetradecahydro-1H-cyclopenta[a]phenanthrene-17-yl)hept-5-enoate having the peaks with 2θ diffraction angles of 15.2°±0.2°, 19.6°±0.2°, 18.5°±0.2°, 18.3°±0.2°, 17.2°±0.2°, 10.8°±0.2°, 21.8°±0.2°, 11.7°±0.2°, 18.1°±0.2°, 19.0°±0.2°, and 16.0°±0.2° in X-ray powder diffraction pattern (XRPD).

At this time, the crystalline form VII can further include the peaks with 2θ diffraction angles of 26.0°±0.2°, 28.5°±0.2°, 21.3°±0.2°, 24.6°±0.2°, 30.3°±0.2°, 23.0°±0.2°, 31.4°±0.2°, 20.4°±0.2°, 14.3°±0.2°, 33.4°±0.2°, 23.3°±0.2°, 9.0°±0.2°, 25.8°±0.2°, 32.3°±0.2°, 11.4°±0.2°, 8.7°±0.2°, 40.7°±0.2°, 36.4°±0.2°, 12.6°±0.2°, 49.1°±0.2°, 34.6°±0.2°, 37.6°±0.2°, and 24.2°±0.2°.

For example, the crystal line form VII can be a crystalline form having the characteristic peaks with 2θ diffraction angles of 8.7°±0.2°, 9.0°±0.2°, 10.8°±0.2°, 11.4°±0.2°, 11.7°±0.2°, 12.6°±0.2°, 14.3°±0.2°, 15.2°±0.2°, 16.0°±0.2°, 17.2°±0.2°, 18.1°±0.2°, 18.3°±0.2°, 18.5°±0.2°, 19.0°±0.2°, 19.6°±0.2°, 20.4°±0.2°, 21.3°±0.2°, 21.8°±0.2°, 23.0°±0.2°, 23.3°±0.2°, 24.2°±0.2°, 24.6°±0.2°, 25.8°±0.2°, 26.0°±0.2°, 28.5°±0.2°, 30.3°±0.2°, 31.4°±0.2°, 32.3°±0.2°, 33.4°±0.2°, 34.6°±0.2°, 36.4°±0.2°, 37.6°±0.2°, 40.7°±0.2°, and 49.1°±0.2° having a relative intensity (I/I$_0$) of 10% or more.

In one aspect of the present invention, the present invention provides a novel crystalline form VIII of the compound represented by (E)-methyl 6-((3S,8S,9S,10R,13S,14S,17R)-3-(((2S,5S,6R)-5-acetoxy-6-(acetoxymethyl)-5,6-dihydro-2H-pyran-2-yl)oxy)-10,13-dimethyl-2,3,4,7,8,9,10,11,12,13,14,15,16,17-tetradecahydro-1H-cyclopenta[a]phenanthrene-17-yl)hept-5-enoate having the peaks with 2θ diffraction angles of 22.4°±0.2° and 20.5°±0.2° in X-ray powder diffraction pattern (XRPD).

At this time, the crystalline form VIII can further include the peaks with 2θ diffraction angles of 16.3°±0.2°, 18.0°±0.2°, 18.9°±0.2°, 19.6°±0.2°, 21.6°±0.2°, and 36.1°±0.2.

For example, the crystal line form VIII can be a crystalline form having the characteristic peaks with 2θ diffraction angles of 16.3°±0.2°, 18.0°±0.2°, 18.9°±0.2°, 19.6°±0.2°, 20.5°±0.2°, 21.6°±0.2°, 22.4°±0.2°, and 36.1°±0.2° having a relative intensity (I/I$_0$) of 10% or more.

In one aspect of the present invention, the present invention provides a novel crystalline form IX of the compound represented by (E)-methyl 6-((3S,8S,9S,10R,13S,14S,17R)-3-(((2S,5S,6R)-5-acetoxy-6-(acetoxymethyl)-5,6-dihydro-2H-pyran-2-yl)oxy)-10,13-dimethyl-2,3,4,7,8,9,10,11,12,13,14,15,16,17-tetradecahydro-1H-cyclopenta[a]phenanthrene-17-yl)hept-5-enoate having the peaks with 2θ diffraction angles of 18.2°±0.2°, 17.3°±0.2°, 11.5°±0.2°, 18.8°±0.2°, 26.0°±0.2°, 19.5°±0.2°, and 16.0°±0.2° in X-ray powder diffraction pattern (XRPD).

At this time, the crystalline form IX can further include the peaks with 2θ diffraction angles of 35.2°±0.2°, 34.1°±0.2°, 20.1°±0.2°, 24.6°±0.2°, 21.8°±0.2°, 23.2°±0.2°, 14.9°±0.2°, 11.7°±0.2°, 34.5°±0.2°, 31.3°±0.2°, 37.0°±0.2°, 27.8°±0.2°, 28.6°±0.2°, 14.2°±0.2°, 33.1°±0.2°, 5.5°±0.2°, 37.5°±0.2°, 8.9°±0.2°, and 12.4°±0.2°.

For example, the crystalline form IX can be a crystalline form having the characteristic peaks with 2θ diffraction angles of 5.5°±0.2°, 8.9°±0.2°, 11.5°±0.2°, 11.7°±0.2°, 12.4°±0.2°, 14.2°±0.2°, 14.9°±0.2°, 16.0°±0.2°, 17.3°±0.2°, 18.2°±0.2°, 18.8°±0.2°, 19.5°±0.2°, 20.1°±0.2°, 21.8°±0.2°, 23.2°±0.2°, 24.6°±0.2°, 26.0°±0.2°, 27.8°±0.2°, 28.6°±0.2°, 31.3°±0.2°, 33.1°±0.2°, 34.1°±0.2°, 34.5°±0.2°, 35.2°±0.2°, 37.0°±0.2°, and 37.5°±0.2°, having a relative intensity (I/I$_0$) of 10% or more.

In one aspect of the present invention, the present invention provides a novel crystalline form X of the compound represented by (E)-methyl 5-((3S,8S,9S,10R,13S,14S,17R)-3-(((2S,5S,6R)-5-acetoxy-6-(acetoxymethyl)-5,6-dihydro-2H-pyran-2-yl)oxy)-10,13-dimethyl-2,3,4,7,8,9,10,11,12,13,14,15,16,17-tetradecahydro-1H-cyclopenta[a]phenanthrene-17-yl)hept-5-enoate having the peaks with 2θ diffraction angles of 18.6°±0.2°, 21.9°±0.2°, 19.8°±0.2°, 17.2°±0.2°, 17.4°±0.2°, 19.7°±0.2°, 15.4°±0.2°, and 28.9°±0.2° in x-ray powder diffraction pattern (XRPD).

At this time, the crystalline form X can further include the peaks with 2θ diffraction angles of 11.5°±0.2°, 36.1°±0.2°, 17.8°±0.2°, 24.8°±0.2°, and 31.6°±0.2°.

For example, the crystalline form X can be a crystalline form having the characteristic peaks with 2θ diffraction angles of 11.5°±0.2°, 15.4°±0.2°, 17.2°±0.2°, 17.4°±0.2°, 17.8°±0.2°, 18.6°±0.2°, 19.1°±0.2°, 19.8°±0.2°, 21.9°±0.2°, 24.8°±0.2°, 28.9°±0.2°, 31.6°±0.2°, and having a relative intensity (I/I$_0$) of 10% or more.

In one aspect of the present invention, the present invention provides a novel crystalline form X I of the compound represented toy (E)-methyl 6-(3S,8S,9S,10R,13S,14S,17R)-3-(((2S,5S,6R)-5-acetoxy-6-(acetoxymethyl)-5,6-dihydro-2H-pyran-2-yl)oxy)-10,13-dimethyl-2,3,4,7,8,9,10,11,12,13,14,15,16,17-tetradecahydro-1H-cyclopenta[a]phenanthrene-17-yl)hept-5-enoate having the peaks with 2θ diffraction angles of 15.0°±0.2°, 19.3°±0.2°, 21.8°±0.2°, 18.2°±0.2°, 17.3°±0.2°, and 35.0°±0.2°, in X-ray powder diffraction pattern (XRPD).

In another aspect of the present invention, the present invention provides a pharmaceutical composition for preventing or treating vascular leakage disease comprising any one of the compounds and the novel crystalline forms I to V of the compound. Or, the present invention provides a pharmaceutical composition for preventing or treating vascular leakage disease comprising any one of the crystalline forms I to X I of the compound.

At this time, the vascular leakage disease can be diabetes, inflammation, retinopathy, diabetic retinopathy, macular degeneration, glaucoma, stenosis, restenosis, arteriosclerosis, atherosclerosis, brain edema, arthritis, arthropathy, uveitis, inflammatory bowel disease, macular edema, cancer, immune anticancer adjuvant, hereditary angioedema (HAE), hyperlipidemia, ischemic disease, diabetic foot ulceration, pulmonary hypertension, acute lung injury, myocardial ischemia, heart failure, acute lower limb ischemia, myocardial infarction, stroke, ischemia or reperfusion injury, VLS (vascular leakage syndrome), edema, transplant rejection, burns, acute or adult respiratory distress syndrome (ARDS), sepsis or autoimmune disease.

MODE FOR INVENTION

Hereinafter, the present invention will be described in detail by the following examples and experimental examples.

However, the following examples and experimental examples are only for illustrating the present invention, and the contents of the present invention are not limited thereto.

EXPERIMENTAL METHODS

1. X-ray Powder Diffractometer (XRPD)

The X-ray powder diffraction (XRPD) pattern was obtaine d on a Shimadzu XRD-6000 instrument.
Setting
Tube: Cu: K-α (λ=1.54056 Å)
Generator: Voltage: 40 kV; Current: 30 mA
Scan Scope: 3~50 deg. Scanning rate: 5 deg./min 2. Differential Scanning Calorimeter (DSC)

Samples of compounds (~1 mg) were tested in an aluminum pan pinhole under nitrogen purge.
Setting
Ramp rate: 20° C./min over the range 30° C.~300° C.
Nitrogen purge: 50 mL/min
Samples: About 1 mg 3. Thermal Gravimetric Analysis (TGA)

Samples of compounds (4~6 mg) were weighed into the pan, and heated under nitrogen purge.
Setting
Ramp rate: 20° C./min over the range 30° C.~300° C.
Nitrogen purge: 50 mL/min
Samples: About 5 mg 4. Dynamic Vapor Sorption (DVS)

Around 10 mg of samples were used to test its moisture sorption/desorption profiles.
Setting
Temperature: 25° C.
Equilibrium: dm/dt: 0.01%/min
Relative Humidity (RH) measurement stepscope: 0%~95%~0% RH
Relative Humidity (RH) measurement step: 5% RH
Samples: 10-20 mg
Hygroscopicity Classification
Hygroscopicity: Water Sorption Criterion
Deliquescent: Sufficient water is absorbed to form a liquid.
Very hygroscopic: W %≥15%
Hygroscopic: W %≥2%
Slightly hygroscopic: W %≥0.2%
Non-hygroscopic: W %<0.2%
25±1° C., 80±2% RH 5. Polarized Light Microscope (PLM)

Samples dispersed in silicone oil were observed using ocular lens: 10X and objective lens: 10X or 5X under crossed polarizers, and recorded by camera/computer system with magnification scale.

6. High Performance Liquid Chromatography (HPLC)

Column: Agilent Zorbax Rx C8, 4.6 mm×250 mm, 5.0 μm
Moving phase: 85% acetonitrile
Flow rate: 1.0 mL/rain
Wavelength: 205 nm
Injection volume: 10 λL
Column temperature: 30° C.
Diluent: 100% acetonitrile <Preparative Example 1> Preparation of Compound 1

The compound 1 represented by the following formula 1 can be prepared by the preparation method described in Korean Patent Application No. 10-2019-0166864 (unpublished). Particularly, the compound can be prepared by the method according to the following reaction formula 1 or 2.

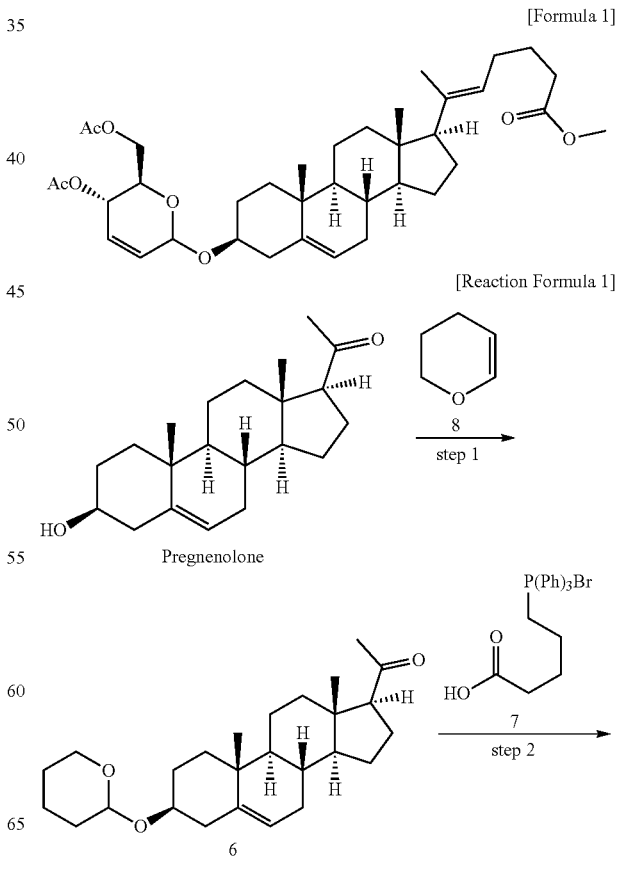

[Formula 1]

[Reaction Formula 1]

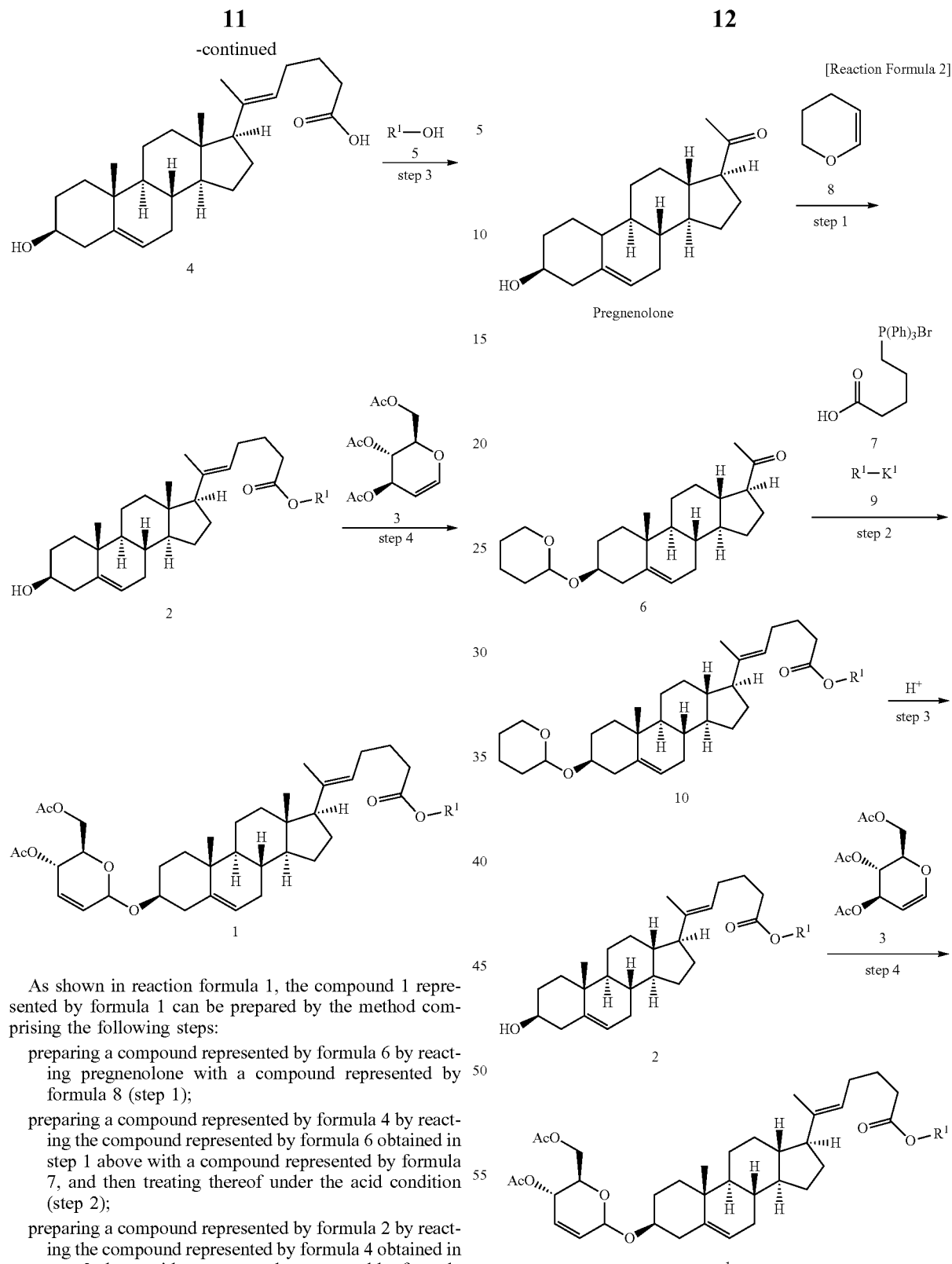

As shown in reaction formula 1, the compound 1 represented by formula 1 can be prepared by the method comprising the following steps:

preparing a compound represented by formula 6 by reacting pregnenolone with a compound represented by formula 8 (step 1);

preparing a compound represented by formula 4 by reacting the compound represented by formula 6 obtained in step 1 above with a compound represented by formula 7, and then treating thereof under the acid condition (step 2);

preparing a compound represented by formula 2 by reacting the compound represented by formula 4 obtained in step 2 above with a compound represented by formula 5 (step 3); and preparing a compound represented by formula 1 by reacting the compound represented by formula 2 obtained in step 3 above with a compound represented by formula 3 in the presence of a catalyst (step 4).

At this time, $R^1$ in reaction formula 1 is straight or branched $C_{1-10}$ alkyl.

As shown in reaction formula 2, the compound 1 represented by formula 1 can be prepared by the method comprising the following steps:

preparing a compound represented by formula 6 by reacting pregnenolone with a compound represented by formula 8 (step 1);

preparing a compound represented by formula 10 by reacting a compound represented by formula 6, a compound represented by formula 7, and a compound represented by formula 9 (step 2);

preparing a compound represented by formula 2 by reacting the compound represented by formula 10 obtained in step 2 above with an acid substance (step 3); and preparing a compound represented by formula 1 by reacting the compound represented by formula 2 obtained in step 3 above with a compound represented by formula 3 in the presence of a catalyst (step 4).

At this time, $R^1$ is straight or branched $C_{1-10}$ alkyl; and $X^1$ is halogen.

On the other hand, the compound 1 represented by formula 1 used in the following examples and experimental examples of the present invention was prepared by the method shown in reaction formula 3 below.

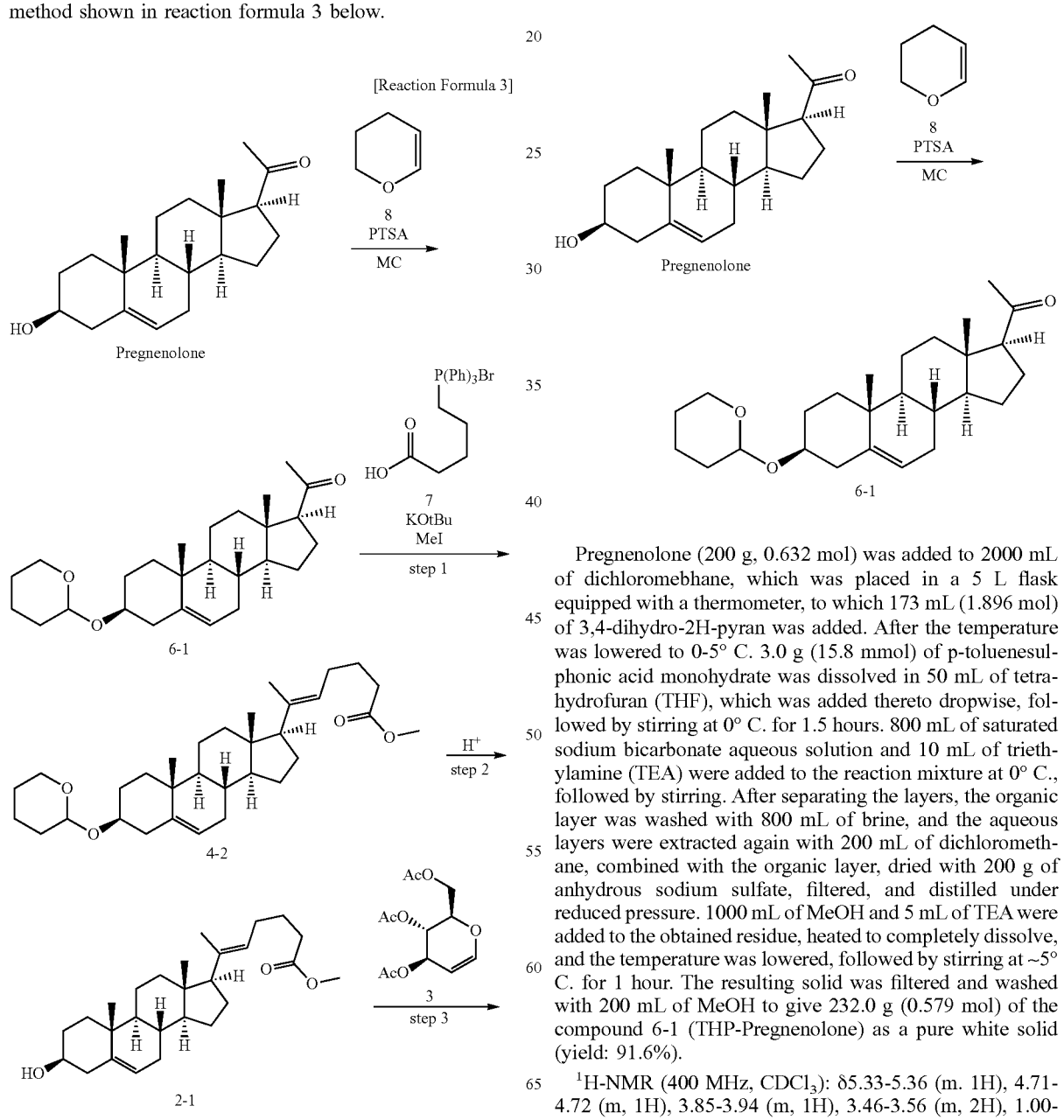

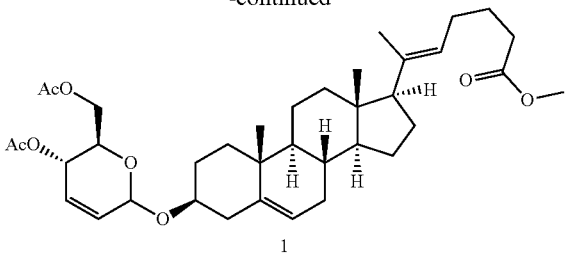

The specific preparation process is as follows.

Step 1: Preparation of Compound 6-1

Pregnenolone (200 g, 0.632 mol) was added to 2000 mL of dichloromebhane, which was placed in a 5 L flask equipped with a thermometer, to which 173 mL (1.896 mol) of 3,4-dihydro-2H-pyran was added. After the temperature was lowered to 0-5° C. 3.0 g (15.8 mmol) of p-toluenesulphonic acid monohydrate was dissolved in 50 mL of tetrahydrofuran (THF), which was added thereto dropwise, followed by stirring at 0° C. for 1.5 hours. 800 mL of saturated sodium bicarbonate aqueous solution and 10 mL of triethylamine (TEA) were added to the reaction mixture at 0° C., followed by stirring. After separating the layers, the organic layer was washed with 800 mL of brine, and the aqueous layers were extracted again with 200 mL of dichloromethane, combined with the organic layer, dried with 200 g of anhydrous sodium sulfate, filtered, and distilled under reduced pressure. 1000 mL of MeOH and 5 mL of TEA were added to the obtained residue, heated to completely dissolve, and the temperature was lowered, followed by stirring at ~5° C. for 1 hour. The resulting solid was filtered and washed with 200 mL of MeOH to give 232.0 g (0.579 mol) of the compound 6-1 (THP-Pregnenolone) as a pure white solid (yield: 91.6%).

$^1$H-NMR (400 MHz, CDCl$_3$): δ5.33-5.36 (m. 1H), 4.71-4.72 (m, 1H), 3.85-3.94 (m, 1H), 3.46-3.56 (m, 2H), 1.00-2.55 (m, 32H), 0.62 (S, 3H).

Step 2: Preparation of Compound 4-2

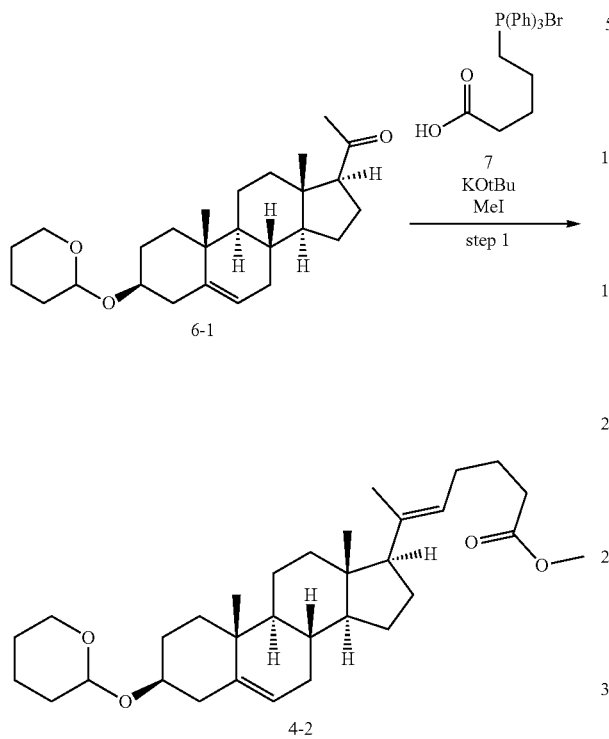

After installing a condenser, heating mantle, and mechanical stirrer in a 5 L reactor, it was heated to 119° C. (external temperature), and cooled to room temperature while flowing nitrogen for 5 minutes, to which 332.5 g (0.75 mol) of 4-(carboxybutyl)triphenyl phosphonium bromide, 168.1 g (1.50 mol) of potassium t-butoxide, 2000 mL of anhydrous toluene and 750 mL of anhydrous tetrahydrofuran were added, followed by stirring for about 2 hours while heating at 119° C. (external temperature, internal mild reflux).

The compound 6-1 (100.0 g, 0.250 mol) was dissolved in 500 mL of anhydrous toluene, which was added to the reaction solution, followed by reaction for about 20 hours.

Upon completion of the reaction, the reaction mixture was cooled to room temperature, to which 320 mL (5.14 mol) of methyl iodide and 1000 mL of acetone were added, followed by stirring at room temperature for 15 hours. The reaction mixture was distilled under reduced pressure to remove most of the organic solvent, to which 1500 mL of ethyl acetate was added to dissolve, followed by washing with 1000 mL of saturated ammonium chloride aqueous solution. The organic layer was washed with 1000 mL of water twice and 1000 mL of brine, dried over 100 g of sodium sulfate, filtered with 80 g of celite, and concentrated.

The obtained residue was dissolved in 2000 ml of methanol, followed by stirring for 13 hours at 10° C. and 1 hour at 4-5° C. The resulting solid was filtered, washed with 200 mL of methanol, and dried in vacuo to give 66.2 g of the compound 4-2 as a white solid (yield: 53.2%).

$^1$H NMR(400 MHz, CDCl$_3$): δ 5.36(t, J=5.80 Hz, 1H), 5.16(t, J=7.00 Hz, 1H), 4.71(m, 1H), 3.93(m, 1H), 3.66(s, 3H), 3.56(m, 2H), 2.37-0.88(m, 38H), 0.54(s, 3H).

Step 3: Preparation of Compound 2-1

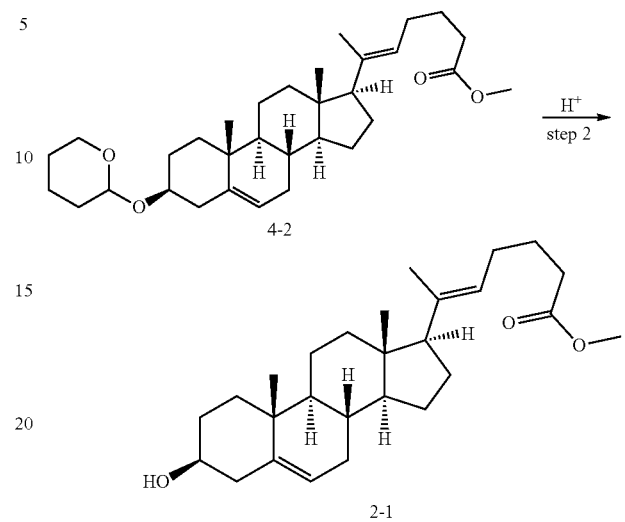

The compound 4-2 (100 g, 0.200 mol), 1000 mL of methanol and 3.82 g (0.020 mol) of p-toluenesulphonic acid mono hydrate were added to a 2 L flask equipped with a thermometer, followed by stirring at 60° C. for 3 hours.

Upon completion of the reaction, the reaction solution was stirred at room temperature. When a solid was formed, the mixture was stirred at room temperature for 30 minutes and stirred at 10° C. for 1 hour. The reaction solution was filtered, washed with 100 mL of cooled methanol, and dried in vacuo to give 61.2 g (0.150 mol) of the compound 2-1 as a white solid (yield: 75.0%).

$^1$H-NMR (400 MHz, CDCl$_3$); δ 5.33-5.35(m, 1H), 5.12-5.16 (m, 1H), 3.66 (s, 3H), 3.50-3.52 (m, 1H), 0.98-2.32 (m, 33H), 0.53 (s, 3H).

Step 4: Preparation of Compound 1

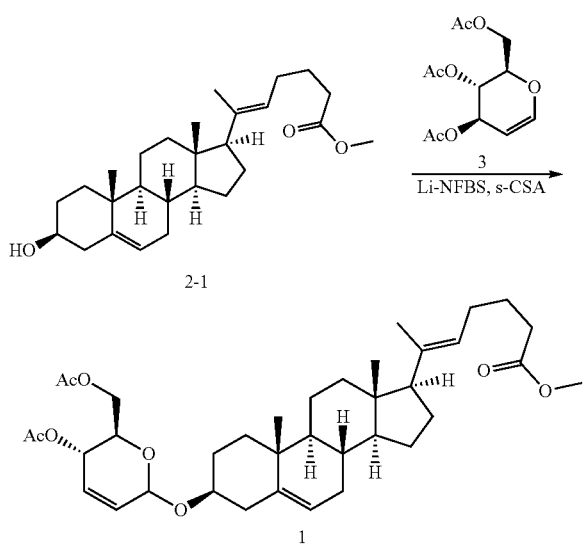

The compound 2-1 (42.0 g, 0.101 mol) and tri i-O-acetyl D-glucal (34.5 g, 0.126 mol) were dissolved in 126 mL of anhydrous toluene and 252 ml of acetonitrile, which were added to a 1 L flask equipped with a thermometer and water bath. While maintaining the temperature at 30-35° C. lithium nonafluoro-1-butylsulfonate (3.87 g, 0.0130 mol) and (s)-camphor sulphonic acid (0.117 g, 0.0005 mol) were added thereto, followed by stirring for 2 hours. Upon completion of the reaction, the reaction solution was quenched with 504 mL of saturated sodium bicarbonate aqueous solution, and extracted with 630 mL of heptane. The organic layer was washed with 504 mL of saturated sodium bicarbonate aqueous solution twice, and 504 mL of brine. The organic layer was stirred after adding 42 g of anhydrous sodium sulfate and 54 g of charcoal, filtered with 34 g of celite, washed with 210 mL of methylene chloride, combined with the filtrate, concentrated and dried in vacuo.

1H-NMR (400 MHz, CDCl$_3$): δ 5.79-5.88 (m, 2H), 5.35-5.36 (m, 1H), 5.27-5.29 (m, 1H), 5.12-5.16 (m, 2H), 4.15-4.24 (m, 3H), 3.66 (s, 3H), 3.54-3.57 (m, 1), 0.91-2.32 (m, 38H), 0.54 (s, 3H).

Stereochemical Analysis of Compound 1

The compound 1 obtained through the reaction formula 3 is present as a mixture of α and β-isomers. At this time, the oily residue was heated and dissolved in 336 mL of ethanol at 50-55° C., followed by stirring at 30° C. when a solid was formed, the temperature was lowered to 0° C., followed by stirring for 30 minutes. The solid was filtered under reduced pressure and dried in vacuo to separate the α-isomer as crystals, and the filtrate was subjected to column chromatography to separate the β-isomer. At this time, the α-isomer was obtained as a solid state, and the purity of the α-isomer was 93.0%.

Figure 1B:
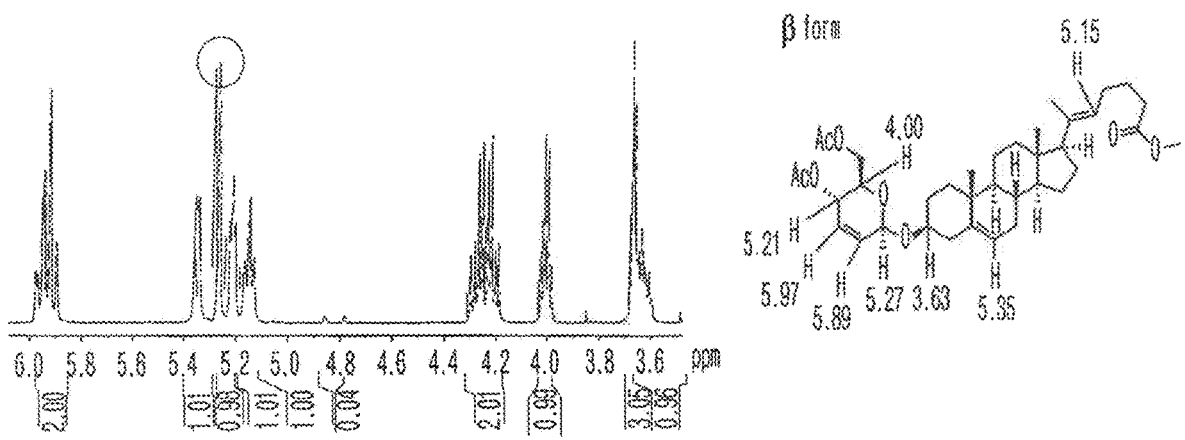
FIG. 1B is a diagram showing the results of NMR analysis to confirm the structures of β-isomer of the compound 1 prepared in Preparative Example 1, and the stereochemical structures of the β-isomer.

The results of NMR performed to confirm the structures of the α- and β-isomers are shown in FIG. 1A and FIG. 1B. As shown in FIG. 1A and FIG. 1B, it was confirmed that the prepared crude compound 1 has the α-isomer or β-isomer having different stereostructures.

On the other hand, the crude compound obtained by the preparation method disclosed in Korean Patent Laid-Open Publication No. 10-2011-0047170 was an oil phase in which α-isomer and β-isomer are mixed, whereas the compound prepared according to the preparation method disclosed in this application was a solid phase of α-isomer.

<Example 1> Preparation of Crystalline form I of Compound 1

About 50 mg of the compound 1 prepared in Preparative Example 1 was dispersed in a solvent with relatively low solubility (water, methanol or ethanol), followed by stirring at room temperature (25° C. for 3 days. The resulting wet solid was separated by centrifugation. The solid was dried at room temperature for 24 hours under reduced pressure. In order to analyze the crystalline form characteristics of the dried solid, the following experiments were performed.

Characteristic Analysis

In order to analyze the characteristics of the crystalline form prepared in Example 1, the crystalline form in the state of white powder was analyzed by solubility assay, X-ray powder diffraction (XRPD), differential scanning calorimetry (DSC), thermal gravimetric analysis (TGA), dynamic vapor sorption (DVS), and polarization microscopy (PLM) according to the methods described in <Experimental Methods>. The results are shown in FIGS. 2 to 6, respectively.

Solubility Assay

Solubility assay was performed by visual observation and manual dilution at room temperature. Particularly, about 4.0 mg of the compound 1 prepared in Preparative Example 1 was weighed in a 4.0 mL glass vial, to which a solvent was sequentially added until no particles were observed with the naked eye (i.e., all dissolved) or the particles remained (i.e., not dissolved) even after adding 4 mL of the solvent for example, total volume of 200, 500, 1000, 2000, or 4000 μL). The total amount of the solvent was recorded to calculate the solubility for each solvent. The results are shown in Table 1 below.

TABLE 1

| Solvent | Solubility (mg/mL) |
|---|---|
| Water (H$_2$O) | <1 |
| Methanol (MeOH) | 6.9~8.2 |
| Ethanol (EtOH) | 5.1~6.4 |
| Isopropanol (IPA) | 5.1~6.8 |
| Acetonitrile (ACN) | >82.6 |
| Acetone | >100 |
| Methyl ethyl ketone (MEK) | >100 |
| Ethyl acetate (EtOAc) | >100 |
| Isopropyl acetate (iPrOAc) | >100 |
| Methyl tert-butyl ether (MTBE) | >85.4 |
| 1-butanol | 26~52 |
| n-propanol | 26.1~52.1 |
| Butyl acetate | >88.6 |
| Tetrahydrofuran (THF) | >76 |
| Toluene | >83 |
| n-heptane | 6.3~8.8 |
| Dichloromethane (DCM) | >100 |
| Dimethyl sulfoxide (DMSO) | 30~45 |
| N,N-dimethylformamide (DMF) | >100 |
| Cyclohexane | 26~40 |
| 1,4-dioxane | >100 |
| Isopropyl ether | 65.2~130.4 |
| 2-methyl-tetrahydrofuran | >93.2 |
| Chloroform | >100 |
| Anisole | >100 |
| Petroleum ether | 11.5~15.3 |

X-ray Powder Diffraction (XRPD)

Figure 2:
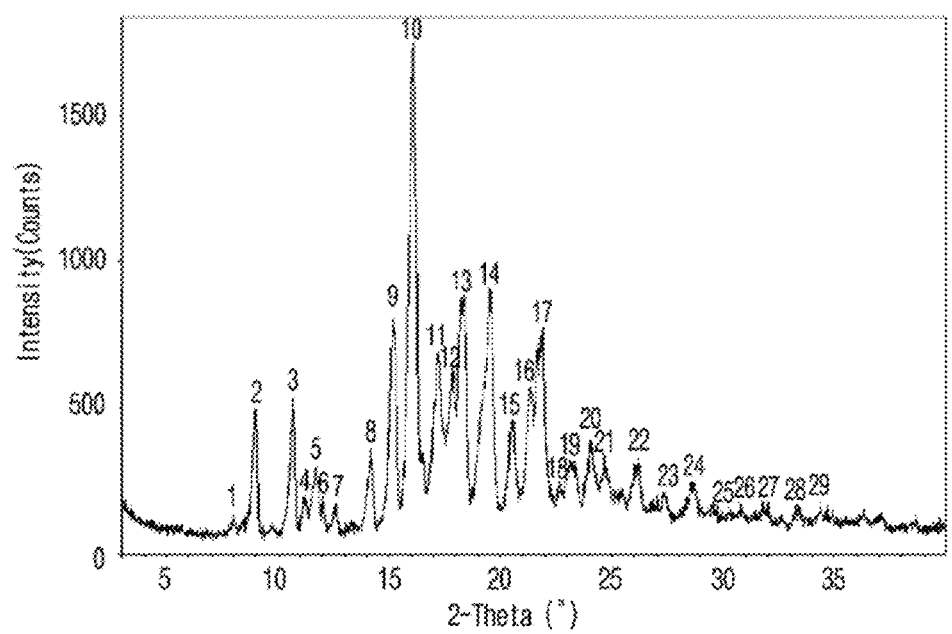
FIG. 2 is a graph showing the results of X-ray powder diffraction (XRPD) of the crystalline form I according to Example 1.
Figure 3:
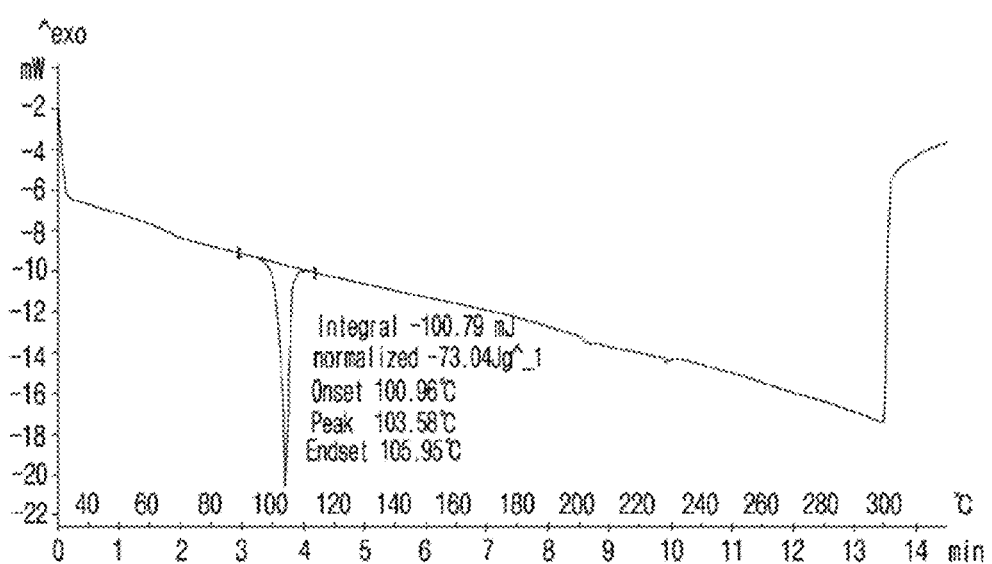
FIG. 3 is a graph showing the results of differential scanning calorimetry (DSC) of the crystalline form I according to Example 1.
Figure 4:
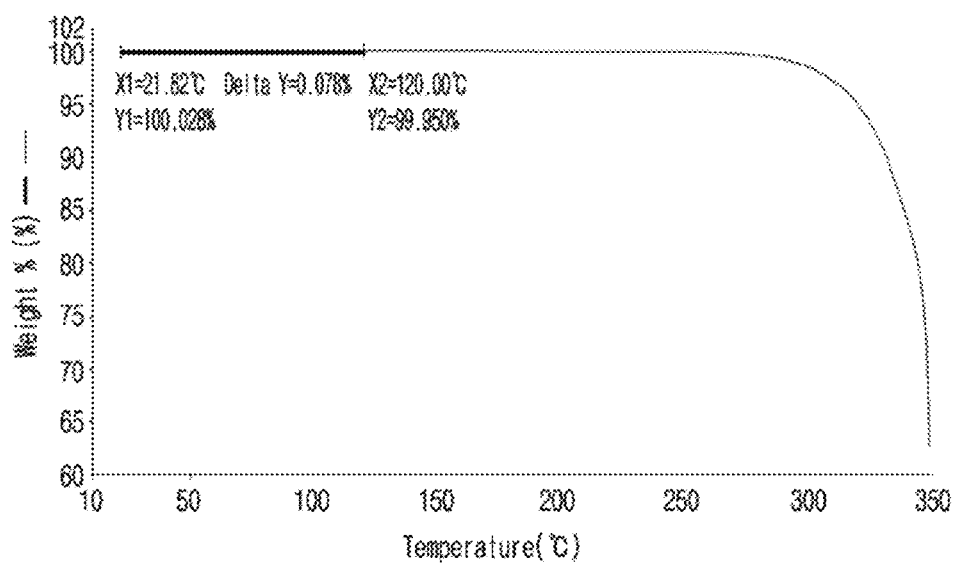
FIG. 4 is a graph showing the results of thermal gravimetric analysis (TGA) of the crystalline form I according to Example 1.
Figure 5:
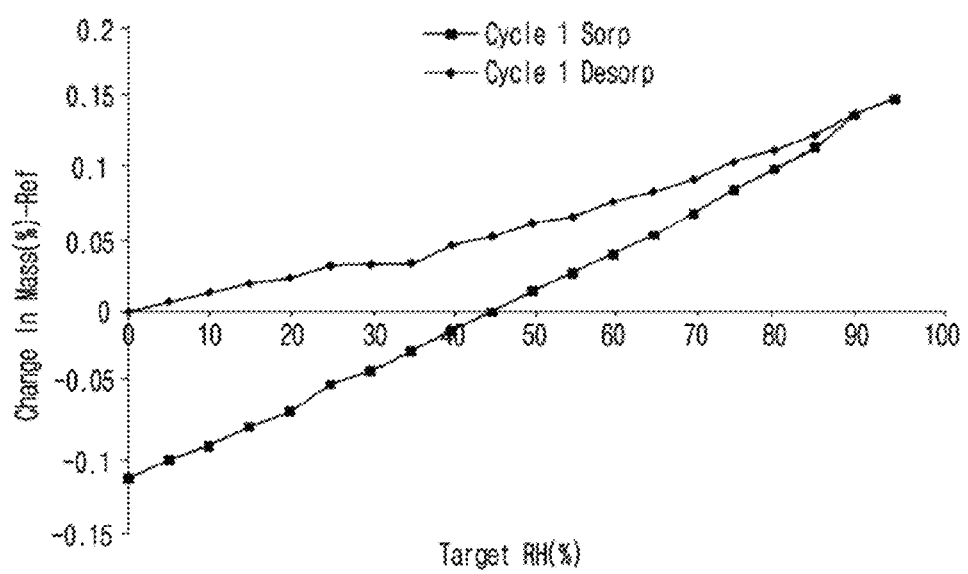
FIG. 5 is a graph showing the results of dynamic vapor sorption (DVS) of the crystalline form I according to Example 1.
Figure 6:
FIG. 6 is a photograph of the crystalline form I according to Example 1 taken with a polarization microscope (PLM).

The peaks having a relative intensity (I/I$_0$) of 10% or more in XRPD spectrum of the crystalline form of FIG. 2 are shown in Table 2 below.

TABLE 2

| No. | 2θ (±0.2°) | d value (A) | I/I$_0$ (%) |
|---|---|---|---|
| 1 | 8.9 | 9.8 | 27.4 |
| 2 | 10.7 | 8.2 | 29.0 |
| 3 | 11.7 | 7.5 | 13.4 |
| 4 | 14.1 | 6.2 | 17.8 |
| 5 | 15.1 | 5.8 | 42.3 |
| 6 | 16.0 | 5.5 | 100.0 |
| 7 | 17.2 | 5.1 | 22.4 |
| 8 | 17.8 | 4.9 | 25.1 |
| 9 | 18.3 | 4.8 | 44.6 |
| 10 | 19.5 | 4.5 | 47.7 |
| 11 | 20.5 | 4.3 | 17.3 |
| 12 | 21.3 | 4.1 | 23.5 |
| 13 | 21.9 | 4.0 | 38.2 |
| 14 | 24.0 | 3.6 | 13.3 |
| 15 | 24.6 | 3.6 | 11.1 |
| 16 | 26.1 | 3.4 | 10.8 |

2θ: diffraction angle, d: distance between crystal faces, I/I₀ (%): relative intensity (I: intensity of each peak; I₀: intensity of highest peak)

In general, the error range of the diffraction angle (2θ) in X-ray powder diffraction is within ±0.2°. Therefore, it should be understood that the values of the diffraction angles also include the values within the range of about ±0.2°. Accordingly, the present invention includes not only the crystals having the same diffraction angle and peak in X-ray powder diffraction, but also the crystals having the diffraction angle consistent with the value indicated by the error range of ±0.2°.

When the relative intensity (I/I₀) of the peak was 10% or more, the peak had the diffraction angles of 8.9°, 10.7°, 11.7°, 14.1°, 15.1°, 16.0°, 17.2°, 17.8°, 18.3°, 19.5°, 20.5°, 21.3°, 21.9°, 24.0°, 24.6°, and 26.1° (2θ±0.2°). The crystalline form of the compound 1 having such a crystalline form is called the crystalline form I.

Dynamic Vapor Sorption (DVS)

The DVS graph analysis results of the crystalline form I are shown in Table 3 below.

TABLE 3

| Target RH (%) | Mass change (%) | | |
|---|---|---|---|
| | Sorption | Desorption | Hysteresis |
| 0.0 | 0.0000 | −0.1124 | |
| 5.0 | 0.0070 | −0.1004 | −0.1074 |
| 10.0 | 0.0131 | −0.0904 | −0.1034 |
| 15.0 | 0.0191 | −0.0773 | −0.0964 |
| 20.0 | 0.0231 | −0.0673 | −0.0906 |
| 25.0 | 0.0311 | −0.0492 | −0.0803 |
| 30.0 | 0.0321 | −0.0402 | −0.0723 |
| 35.0 | 0.0331 | −0.0261 | −0.0592 |
| 40.0 | 0.0452 | −0.0131 | −0.0582 |
| 45.0 | 0.0512 | 0.0000 | −0.0512 |
| 50.0 | 0.0602 | 0.0141 | −0.0462 |
| 55.0 | 0.0642 | 0.0261 | −0.0381 |
| 60.0 | 0.0743 | 0.0392 | −0.0351 |
| 65.0 | 0.0813 | 0.0522 | −0.0291 |
| 70.0 | 0.0893 | 0.0663 | −0.0231 |
| 75.0 | 0.1014 | 0.0823 | −0.0191 |
| 80.0 | 0.1094 | 0.0964 | −0.0131 |
| 85.0 | 0.1195 | 0.1114 | −0.0080 |
| 90.0 | 0.1335 | 0.1325 | −0.0010 |
| 95.0 | 0.1436 | 0.1436 | |

From the XRPD results above, it was confirmed that the crystalline form I of the compound 1 prepared in Example 1 according to the present invention had excellent crystallinity. From the TGA results, it was confirmed that the crystalline form 1 of the compound 1 had a mass loss of 0.078% while heating from room temperature to 120° C. One endothermic peak (100.96° C.) was confirmed through the DSC result graph, which corresponds to the melting point of the crystalline form I of the compound 1. Through the DVS results, 0.11% of water sorption was confirmed at 80% RH, indicating that the crystalline form I of the compound 1 is non-hygroscopic.

<Example 2> Preparation of Crystalline form II of Compound 1

About 50 mg of the compound 1 prepared in Preparative Example 1 was dispersed in isopropanol (1 mL) in a 4 mL glass bottle, followed by stirring at high temperature (50° C.) for 3 days. Then, the glass bottle was cooled in a refrigerator for one day, and no solid precipitate was observed. The glass bottle was continuously stored in a −20° C. refrigerator for 7 days, and the solid precipitate was separated by centrifugation (12000 rpm, 5 minutes). The precipitate was then dried at room temperature for 24 hours in a vacuum oven under reduced pressure. As a result, a thin plate-like lamellar solid or a flaked solid was obtained. In order to analyze the characteristics of the crystalline form of the prepared solid, XRPD was performed according to the method described in <Experimental Methods> 1. X-ray Powder Diffractometer (XRPD), The results are shown in Table 4 and FIG. 7.

Figure 7:
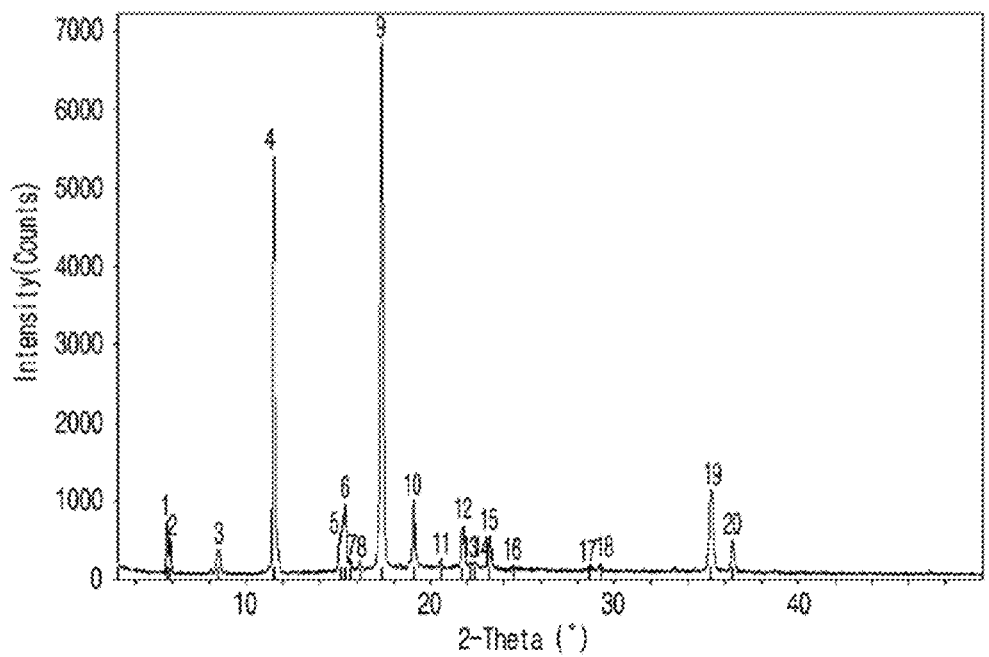
FIG. 7 is a graph showing the results of X-ray powder diffraction (XRPD) of the crystalline form II according to Example 2.

The peaks having a relative intensity (I/I₀) of 10% or more in XRPD spectrum of the crystalline form of FIG. 7 are shown in Table 4 below.

TABLE 4

| No. | 2θ (±0.2°) | d value (A) | I/I₀ (%) |
|---|---|---|---|
| 1 | 5.7 | 15.4 | 10.7 |
| 2 | 11.4 | 7.6 | 78.9 |
| 3 | 15.3 | 5.7 | 13.8 |
| 4 | 17.3 | 5.1 | 100.0 |
| 5 | 19.0 | 4.6 | 14.7 |
| 6 | 35.2 | 2.5 | 16.8 |

2θ: diffraction angle, d: distance between crystal faces, I/I₀ (%): relative intensity (I: intensity of each peak; I₀: intensity of highest peak)

When the relative intensity (I/I₀) of the peak was 10% or more, the peak had the diffraction angles of 5.7°, 11.4°, 15.3°, 17.3°, 19.0°, and 35.2°(2θ±0.2°) The crystalline form of the compound 1 having such a crystalline form is called the crystalline form II.

<Example 3> Preparation of Crystalline form III of Compound 1

Figure 8:
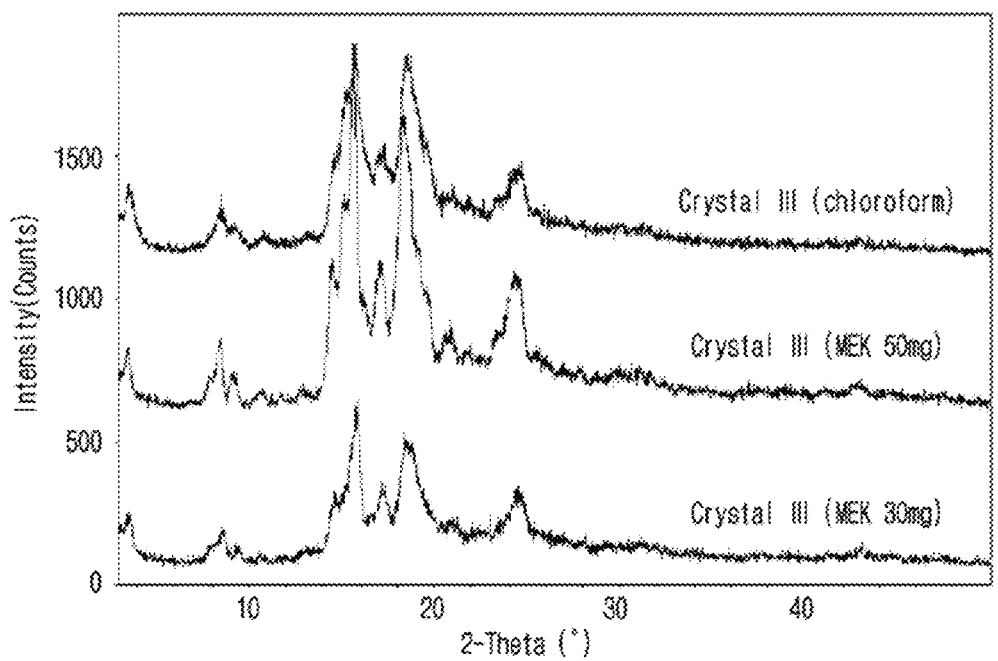
FIG. 8 is a graph showing the results of X-ray powder diffraction (XRPD) of the crystalline form III according to Example 3 prepared in MEK (30 mg, 50 mg) or chloroform (50 mg) solvent.

About 50 mg of the compound 1 prepared in Preparative Example 1 was completely dissolved in MEK or chloroform, a relatively good solvent, at room temperature, and then the reaction vessel was covered with an aluminum foil having a small hole. Then, it was allowed to evaporate naturally for 1 week at room temperature, and as a result, a little solid was precipitated. It was further dried at 40° C. for 24 hours under reduced pressure. In order to analyze the characteristics of the crystalline form of the prepared solid, XRPD was performed according to the method described in <Experimental Methods> 1. X-ray Powder Diffractometer (XRPD). The results are shown in FIG. 8. In addition, the crystalline form prepared under the same conditions, except that about 30 mg of MEK solvent was used, was analyzed by XRPD and the results are shown in FIG. 8.

The peaks having a relative intensity (I/I₀) of 10% or more in XRPD spectrum (solvent: 50 mg of MEK) of the crystalline form of FIG. 8 are shown in Table 5 below.

TABLE 5

| No. | 2θ (±0.2°) | d value (A) | I/I₀ (%) |
|---|---|---|---|
| 1 | 3.5 | 25.0 | 20.2 |
| 2 | 8.5 | 10.3 | 26.5 |
| 3 | 9.0 | 9.7 | 12.5 |
| 4 | 9.3 | 9.4 | 14.4 |
| 5 | 14.4 | 6.1 | 63.9 |
| 6 | 15.0 | 5.8 | 24.9 |
| 7 | 15.6 | 5.6 | 100.0 |

TABLE 5-continued

| No. | 2θ (±0.2°) | d value (A) | I/I₀ (%) |
|---|---|---|---|
| 8 | 16.9 | 5.2 | 33.6 |
| 9 | 17.2 | 5.1 | 30.9 |
| 10 | 18.2 | 4.8 | 99.3 |
| 11 | 20.6 | 4.2 | 12.8 |
| 12 | 20.7 | 4.2 | 11.4 |
| 13 | 20.9 | 4.2 | 11.5 |
| 14 | 24.0 | 3.6 | 12.1 |
| 15 | 24.3 | 3.6 | 25.9 |
| 16 | 24.6 | 3.6 | 40.6 |

2θ: diffraction angle, d: distance between crystal faces, I/I₀ (%): relative intensity (I: intensity of each peak; I₀: intensity of highest peak)

When the relative intensity (I/I₀) of the peak was 10% or more, the peak had the diffraction angles of 3.5°, 8.5°, 9.0°, 9.3°, 14.4°, 15.0°, 15.6°, 16.9°, 17.2°, 18.2°, 20.6°, 20.7°, 20.9°, 24.0°, 24.3°, and 24.6°, (2θ±0.2°). The crystalline form of the compound 1 having such a crystalline form is called the crystalline form III.

<Example 4> Preparation of Crystalline form IV of Compound 1

About 50 mg of the compound 1 prepared in Preparative Example 1 was completely dissolved in EtOH (0.8 mL) at 55° C. to prepare a saturated solution, followed by mixing continuously for 30 minutes. Then, the solution was rapidly cooled to low temperature in a −20° C. refrigerator, and stored for 3 days. After separating the prepared solid by centrifugation, it was dried in vacuo at 40° C. overnight. In order to analyze the characteristics of the crystalline form of the prepared solid, XRPD was performed according to the method described in <Experimental Methods> 1. X-ray Powder Diffractometer (XRPD). The results are shown in Table 6 and FIG. 9.

Figure 9:
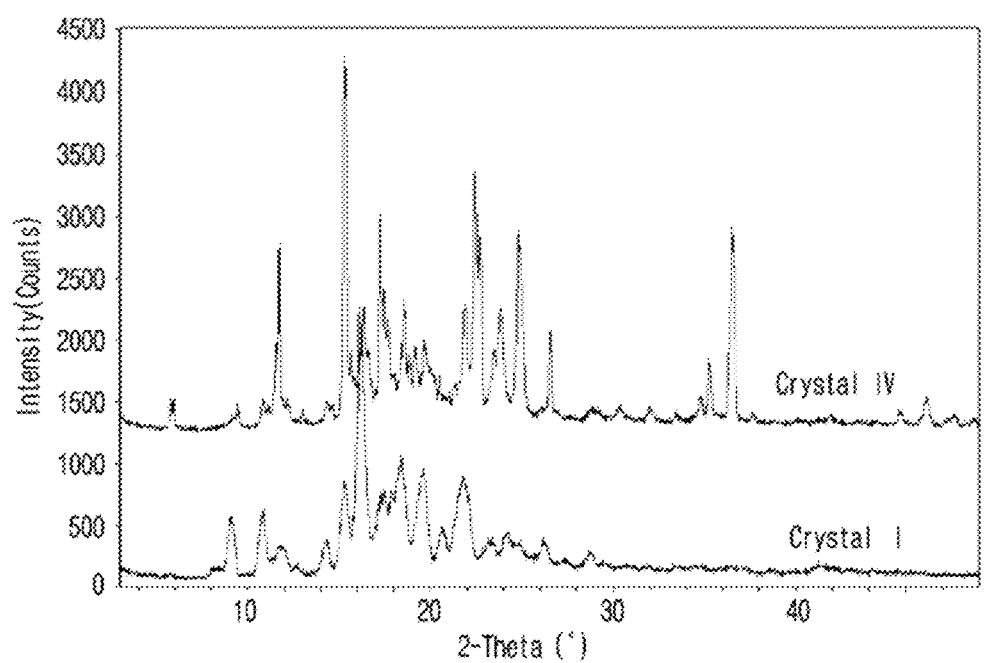
FIG. 9 is a graph showing the results of X-ray powder diffraction (XRPD) comparing the crystalline form IV according to Example 4 with the crystalline form I.

The peaks having a relative intensity (I/I₀) of 10% or more in XRPD spectrum of the crystalline form of FIG. 9 are shown in Table 6 below.

TABLE 6

| No. | 2θ (±0.2°) | d value (A) | I/I₀ (%) |
|---|---|---|---|
| 1 | 5.9 | 14.9 | 10.0 |
| 2 | 10.8 | 8.1 | 10.2 |
| 3 | 11.5 | 7.6 | 22.8 |
| 4 | 11.7 | 7.5 | 50.8 |
| 5 | 14.3 | 6.1 | 10.0 |
| 6 | 15.3 | 5.7 | 100.0 |
| 7 | 15.6 | 5.6 | 19.9 |
| 8 | 16.3 | 5.4 | 34.5 |
| 9 | 16.6 | 5.3 | 23.7 |
| 10 | 17.2 | 5.1 | 59.2 |
| 11 | 17.6 | 5.0 | 31.6 |
| 12 | 18.0 | 4.9 | 16.9 |
| 13 | 18.5 | 4.7 | 36.1 |
| 14 | 18.8 | 4.7 | 22.6 |
| 15 | 19.1 | 4.6 | 24.0 |
| 16 | 19.6 | 4.5 | 25.9 |
| 17 | 20.1 | 4.4 | 16.6 |
| 18 | 21.8 | 4.0 | 35.1 |
| 19 | 22.4 | 3.9 | 69.5 |
| 20 | 22.7 | 3.9 | 53.3 |
| 21 | 23.4 | 3.7 | 23.0 |
| 22 | 23.8 | 3.7 | 34.7 |
| 23 | 24.8 | 3.5 | 54.5 |
| 24 | 26.5 | 3.3 | 28.5 |
| 25 | 34.7 | 2.5 | 11.4 |
| 26 | 35.2 | 2.5 | 20.8 |
| 27 | 36.5 | 2.4 | 55.8 |
| 28 | 47.1 | 1.9 | 10.7 |

2θ: diffraction angle, d: distance between crystal faces, I/I₀ (%): relative intensity (I: intensity of each peak; I₀: intensity of highest peak)

When the relative intensity (I/I₀) of the peak was 10% or more, the peak had the diffraction angles of 5.9°, 10.8°, 11.5°, 11.7°, 14.3°, 15.3°, 15.6°, 16.3°, 16.6°, 17.2°, 17.6°, 18.0°, 18.5°, 18.8°, 19.1°, 19.6°, 20.1°, 21.8°, 22.4°, 22.7°, 23.4°, 23.8°, 24.8°, 26.5°, 34.7°, 35.2°, 36.5°, and 47.1° (2θ±0.2°). The crystalline form of the compound 1 having such a crystalline form is called the crystalline form IV.

<Example 5> Preparation of Crystalline form V of Compound 1

About 50 mg of the compound 1 prepared in Preparative Example 1 was completely dissolved in n-propanol (0.8 mL) at 55° C. to prepare a saturated solution, followed by mixing continuously for 30 minutes. Then, the solution was rapidly cooled to low temperature in a −20° C. refrigerator, and stored for 3 days. After separating the prepared solid by centrifugation, it was dried in vacuo at 40° C. overnight. In order to analyze the characteristics of the crystalline form of the prepared solid, XRPD was performed according to the method described in <Experimental Methods>1. X-ray Powder Diffractometer (XRPD). The results are shown in Table 7 and FIG. 10.

Figure 10:
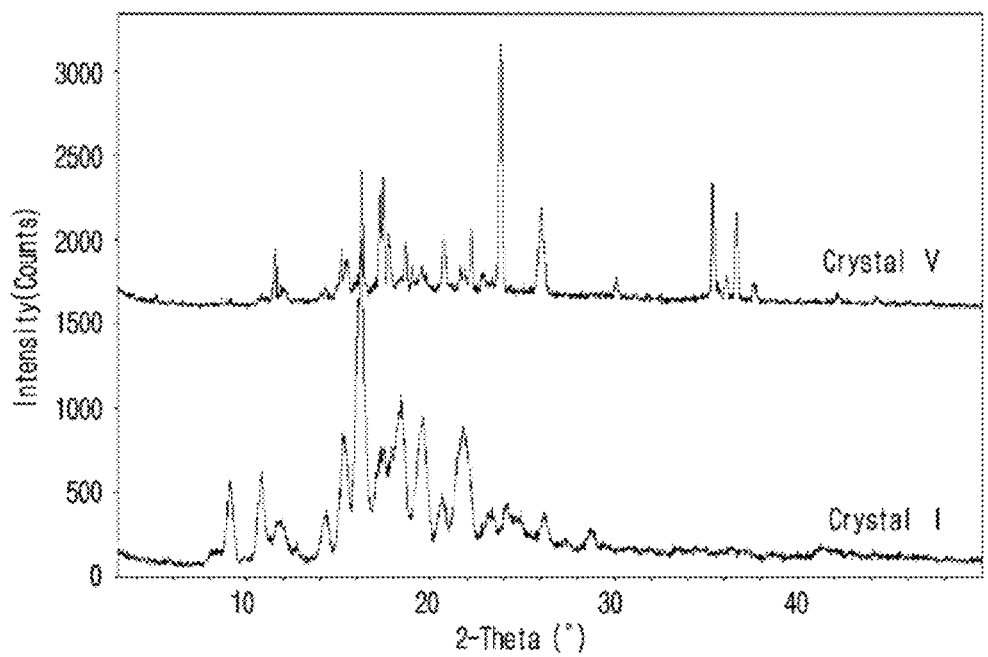
FIG. 10 is a graph showing the results of X-ray powder diffraction (XRPD) comparing the crystalline form V according to Example 5 with the crystalline form I.

The peaks having a relative intensity (I/I₀) of 10% or more in XRPD spectrum of the crystalline form of FIG. 10 are shown in Table 7 below.

TABLE 7

| No. | 2θ (±0.2°) | d value (A) | I/I₀ (%) |
|---|---|---|---|
| 1 | 11.5 | 7.6 | 24.9 |
| 2 | 11.8 | 7.4 | 11.2 |
| 3 | 15.1 | 5.8 | 24.6 |
| 4 | 15.4 | 5.7 | 20.7 |
| 5 | 16.2 | 5.4 | 53.7 |
| 6 | 17.4 | 5.0 | 51.7 |
| 7 | 17.7 | 5.0 | 29.9 |
| 8 | 18.4 | 4.8 | 14.2 |
| 9 | 18.6 | 4.7 | 27.1 |
| 10 | 19.0 | 4.6 | 18.2 |
| 11 | 19.4 | 4.5 | 18.2 |
| 12 | 20.7 | 4.2 | 30.0 |
| 13 | 21.6 | 4.1 | 18.1 |
| 14 | 21.8 | 4.0 | 18.2 |
| 15 | 22.2 | 3.9 | 32.1 |
| 16 | 22.9 | 3.8 | 17.1 |
| 17 | 23.3 | 3.8 | 13.9 |
| 18 | 23.8 | 3.7 | 100.0 |
| 19 | 26.0 | 3.4 | 40.9 |
| 20 | 30.1 | 2.9 | 14.3 |
| 21 | 35.3 | 2.5 | 49.0 |
| 22 | 36.0 | 2.4 | 14.7 |
| 23 | 36.6 | 2.4 | 39.2 |
| 24 | 37.5 | 2.3 | 12.8 |

2θ: diffraction angle, d: distance between crystal faces, I/I₀ (%): relative intensity (I: intensity of each peak; I₀: intensity of highest peak)

When the relative intensity (I/I₀) of the peak was 10% or more, the peak had the diffraction angles of 11.5°, 11.8°, 15.1°, 15.4°, 16.2°, 17.4°, 17.7°, 18.4°, 18.6°, 19.0°, 19.4°, 20.7°, 21.6°, 21.8°, 22.2°, 22.9°, 23.3°, 23.8°, 26.0°, 30.1°, 35.3°, 36.0°, 36.6°, and 37.5°, (2θ±0.2°). The crystalline form of the compound 1 having such a crystalline form is called the crystalline form V.

<Example 6> Preparation of Crystalline form VI of Compound 1

In order to observe whether the crystalline form IV of the compound 1 prepared in Example 4 changed after 2 months at room temperature, the characteristics of the crystalline form IV stored at room temperature for 2 months were analyzed. Particularly, XRPD was performed according to the method described in <Experimental Methods> 1. X-ray Powder Diffractometer (XRPD). As a result, a novel crystalline form having the XRPD pattern different from that of the crystalline form IV was confirmed. The results are shown in Table 8 and FIG. 11.

Figure 11:
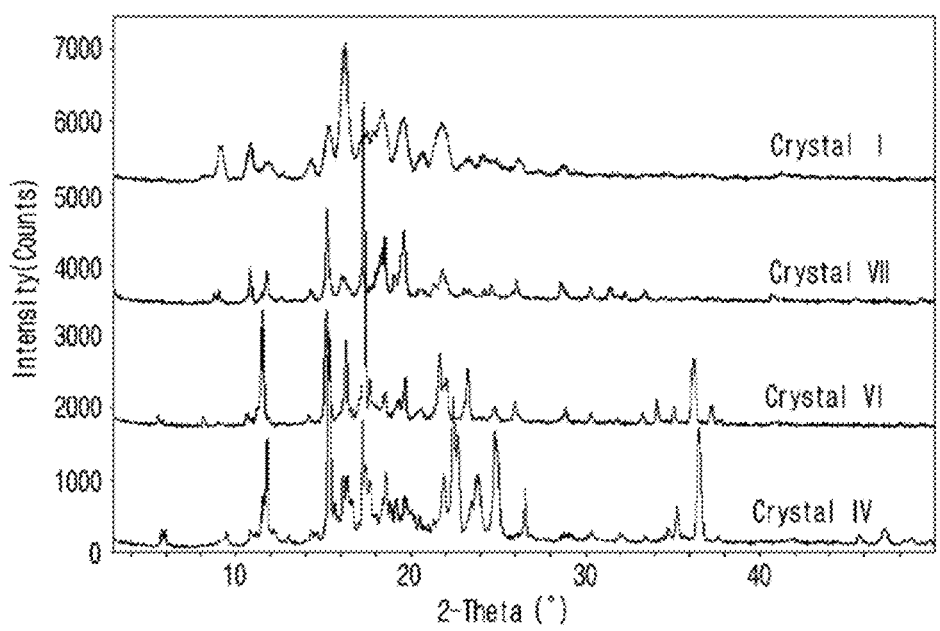
FIG. 11 is a graph showing the results of X-ray powder diffraction (XRPD) comparing the crystalline forms VI and VII according to Examples 6 and 7 with the crystalline forms I and IV.

The peaks having a relative intensity ($I/I_0$) of 10% or more of the crystals after 2 months of the crystalline form IV in XRPD spectrum of the crystalline form of FIG. 11 are shown in Table 8 below.

TABLE 8

| No. | 2θ (±0.2°) | d value (A) | $I/I_0$ (%) |
|---|---|---|---|
| 1 | 11.5 | 7.6 | 36.4 |
| 2 | 15.2 | 5.8 | 36.5 |
| 3 | 16.2 | 5.4 | 27.5 |
| 4 | 17.3 | 5.1 | 100.0 |
| 5 | 17.6 | 5.0 | 15.3 |
| 6 | 18.5 | 4.7 | 11.8 |
| 7 | 19.6 | 4.5 | 16.0 |
| 8 | 21.6 | 4.0 | 23.2 |
| 9 | 22.0 | 4.0 | 16.0 |
| 10 | 23.2 | 3.8 | 18.8 |
| 11 | 36.1 | 2.4 | 21.5 |

2θ: diffraction angle, d: distance between crystal faces, $I/I_0$ (%): relative intensity (I: intensity of each peak; $I_0$: intensity of highest peak)

When the relative intensity ($I/I_0$) of the peak was 10% or more, the peak had the diffraction angles of 11.5°, 15.2°, 16.2°, 17.3°, 17.6°, 18.5°, 19.6°, 21.6°, 22.0°, 23.2°, and 36.1°(2θ±0.2°). The crystalline form of the compound 1 having such a crystalline form is called the crystalline form VI.

<Example 7> Preparation of Crystalline form VII of Compound 1

The experiment was performed in the same manner as described in Example 6 except that the crystalline form IV of the compound 1 prepared in Example 4 was stored at room temperature for 3 months. As a result, a novel crystalline form having the XRPD pattern different from that of the crystalline form IV was confirmed. The results are shown in Table 9 and FIG. 12.

The peaks having a relative intensity ($I/I_0$) of 10% or more of the crystals after 3 months of the crystalline form IV in XRPD spectrum of the crystalline form of FIG. 11 are shown in Table 9 below.

TABLE 9

| No. | 2θ (±0.2°) | d value (A) | $I/I_0$ (%) |
|---|---|---|---|
| 1 | 8.7 | 10.0 | 14.4 |
| 2 | 9.0 | 9.7 | 17.8 |
| 3 | 10.8 | 8.1 | 40.1 |

TABLE 9-continued

| No. | 2θ (±0.2°) | d value (A) | $I/I_0$ (%) |
|---|---|---|---|
| 4 | 11.4 | 7.7 | 14.5 |
| 5 | 11.7 | 7.5 | 36.8 |
| 6 | 12.6 | 7.0 | 11.4 |
| 7 | 14.3 | 6.1 | 19.1 |
| 8 | 15.2 | 5.8 | 100.0 |
| 9 | 16.0 | 5.5 | 32.8 |
| 10 | 17.2 | 5.1 | 41.4 |
| 11 | 18.1 | 4.8 | 36.8 |
| 12 | 18.3 | 4.8 | 56.1 |
| 13 | 18.5 | 4.7 | 72.1 |
| 14 | 19.0 | 4.6 | 34.1 |
| 15 | 19.6 | 4.5 | 77.4 |
| 16 | 20.4 | 4.3 | 19.3 |
| 17 | 21.3 | 4.1 | 25.0 |
| 18 | 21.8 | 4.0 | 38.8 |
| 19 | 23.0 | 3.8 | 21.3 |
| 20 | 23.3 | 3.7 | 18.7 |
| 21 | 24.2 | 3.6 | 1.7 |
| 22 | 24.6 | 3.6 | 23.9 |
| 23 | 25.8 | 3.4 | 16.3 |
| 24 | 26.0 | 3.4 | 28.6 |
| 25 | 28.5 | 3.1 | 26.0 |
| 26 | 30.3 | 2.9 | 21.6 |
| 27 | 31.4 | 2.8 | 20.9 |
| 28 | 32.3 | 2.7 | 14.7 |
| 29 | 33.4 | 2.6 | 18.8 |
| 30 | 34.6 | 2.5 | 11.1 |
| 31 | 36.4 | 2.4 | 12.4 |
| 32 | 37.6 | 2.3 | 10.6 |
| 33 | 40.7 | 2.2 | 13.2 |
| 34 | 49.1 | 1.8 | 11.2 |

2θ: diffraction angle, d: distance between crystal faces, $I/I_0$ (%): relative intensity (I: intensity of each peak; $I_0$: intensity of highest peak)

When the relative intensity ($I/I_0$) of the peak was 10% or more, the peak had the diffraction angles of 8.7°, 9.0°, 10.8°, 11.4°, 11.7°, 12.6°, 14.3°, 15.2°, 16.0°, 17.2°, 18.1°, 18.3°, 18.5°, 19.0°, 19.6°, 20.4°, 21.3°, 21.8°, 23.0°, 32.3°, 33.4°, 34.6°, 36.4°, 37.6°, 40.7°, and 49.1°, (2θ±0.2°). The crystalline form of the compound 1 having such a crystalline form is called the crystalline form VII.

<Example 8> Preparation of Crystalline form VIII of Compound 1

In order to observe whether the crystalline form V of the compound 1 prepared in Example 5 changed after 2 months at room temperature, the characteristics of the crystalline form V stored at room temperature for 2 months were analyzed. Particularly, XRPD was performed according to the method described in <Experimental Methods>1. X-ray Powder Diffractometer (XRPD). As a result, a novel crystalline form having the XRPD pattern different from that of the crystalline form V was confirmed. The results are shown in Table 10 and FIG. 12

Figure 12:
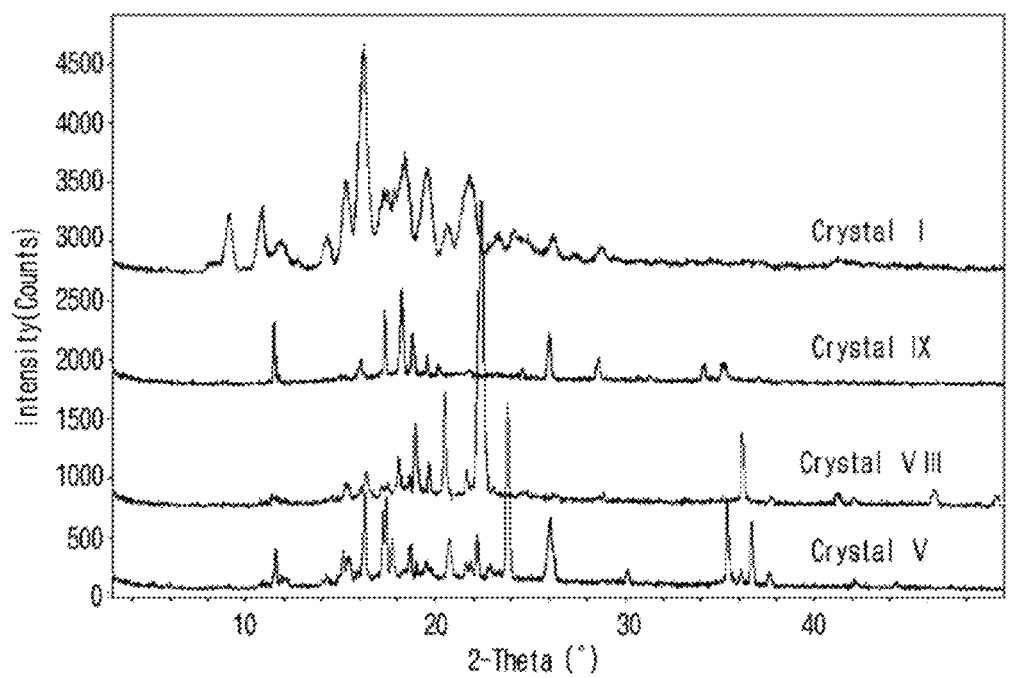
FIG. 12 is a graph showing the results of X-ray powder diffraction (XRPD) comparing the crystalline forms VIII and IX according to Examples 8 and 9 with the crystalline forms I and V.

The peaks having a relative intensity ($I/I_0$) of 10% or more of the crystals after 2 months of the crystalline form V in XRPD spectrum of the crystalline form of FIG. 12 are shown in Table 10 below.

TABLE 10

| No. | 2θ (±0.2°) | d value (A) | $I/I_0$ (%) |
|---|---|---|---|
| 1 | 16.3 | 5.4 | 13.6 |
| 2 | 18.0 | 4.9 | 18.1 |
| 3 | 18.9 | 4.9 | 28.3 |
| 4 | 19.6 | 4.5 | 16.3 |
| 5 | 20.5 | 4.3 | 38.7 |

TABLE 10-continued

| No. | 2θ (±0.2°) | d value (A) | I/I₀ (%) |
|---|---|---|---|
| 6 | 21.6 | 4.0 | 13.9 |
| 7 | 22.4 | 3.9 | 100.0 |
| 8 | 36.1 | 2.4 | 26.0 |

2θ: diffraction angle, d: distance between crystal faces, I/I₀ (%): relative intensity (I: intensity of each peak; I₀: intensity of highest peak)

When the relative intensity (I/I₀) of the peak was 10% or more, the peak had the diffraction angles of 16.3°, 18.0°, 18.9°, 19.6°, 20.5°, 21.6°, 22.4°, and 36.1°(2θ±0.2°). The crystalline form of the compound 1 having such a crystalline form is called the crystalline form VIII.

<Example 9> Preparation of Crystalline form IX of Compound 1

The experiment was performed in the same manner as described in Example 8 except that the crystalline form V of the compound 1 prepared in Example 5 was stored at room temperature for 3 months. As a result, a novel crystalline form having the XRPD pattern different from that of the crystalline form V was confirmed. The results are shown in Table 11 and FIG. 12.

The peaks having a relative intensity (I/I₀) of 10% or more of the crystals after 3 months of the crystalline form V in XRPD spectrum of the crystalline form of FIG. 12 shown in Table 11 below.

TABLE 11

| No. | 2θ (±0.2°) | d value (A) | I/I₀ (%) |
|---|---|---|---|
| 1 | 5.5 | 15.7 | 11.4 |
| 2 | 8.9 | 9.8 | 10.7 |
| 3 | 11.5 | 7.6 | 69.0 |
| 4 | 11.7 | 7.5 | 14.9 |
| 5 | 12.4 | 7.0 | 10.0 |
| 6 | 14.2 | 6.2 | 12.4 |
| 7 | 14.9 | 5.9 | 15.9 |
| 8 | 16.0 | 5.5 | 30.3 |
| 9 | 17.3 | 5.1 | 80.0 |
| 10 | 18.2 | 4.8 | 100.0 |
| 11 | 18.8 | 4.7 | 56.4 |
| 12 | 19.5 | 4.5 | 34.7 |
| 13 | 20.1 | 4.3 | 26.3 |
| 14 | 21.8 | 4.0 | 20.0 |
| 15 | 23.2 | 3.8 | 17.5 |
| 16 | 24.6 | 3.6 | 21.0 |
| 17 | 26.0 | 3.4 | 55.5 |
| 18 | 27.8 | 3.2 | 13.5 |
| 19 | 28.6 | 3.2 | 13.5 |
| 20 | 31.3 | 2.8 | 14.2 |
| 21 | 33.1 | 2.7 | 11.7 |
| 22 | 34.1 | 2.6 | 26.6 |
| 23 | 34.5 | 2.5 | 14.5 |
| 24 | 35.2 | 2.5 | 28.4 |
| 25 | 37.0 | 2.4 | 13.8 |
| 26 | 37.5 | 2.3 | 11.2 |

2θ: diffraction angle, d: distance between crystal faces, I/I₀ (%): relative intensity (I: intensity of each peak; I₀: intensity of highest peak)

When the relative intensity (I/I₀) of the peak was 10% or more, the peak had the diffraction angles of 5.5°, 8.9°, 11.5°, 11.7°, 12.4°, 14.2°, 14.9°, 16.0°, 17.3°, 18.2°, 18.8°, 19.5°, 20.1°, 21.8°, 23.2°, 24.6°, 26.0°, 27.8°, 28.6°, 31.3°, 33.1°, 34.1°, 34.5°, 35.2°, 37.0°, and 37.5°, (2θ±0.2°). The crystalline form of the compound 1 having such a crystalline form is called the crystalline form IX.

<Example 10> Scale up of Crystalline form IV and Preparation of Crystalline form X The scale up of the crystalline form IV prepared in Example 4 was performed as follows. About 100 mg of the compound prepared in Preparative Example 1 was completely dissolved in EtOH (1.6 mL) at 55° C. to prepare a saturated solution, followed by mixing continuously for 30 minutes. Then, the solution was rapidly cooled to low temperature in a −20° C. refrigerator, and stored for 3 days. After separating the prepared solid by centrifugation, it was dried in vacuo at 40° C. overnight. In order to analyze the characteristics of the crystalline form of the prepared solid, XRPD was performed according to the method described in <Experimental Methods>1. X-ray Powder Diffractometer (XRPD). The results are shown in Table 12 and FIG. 13.

Figure 13:
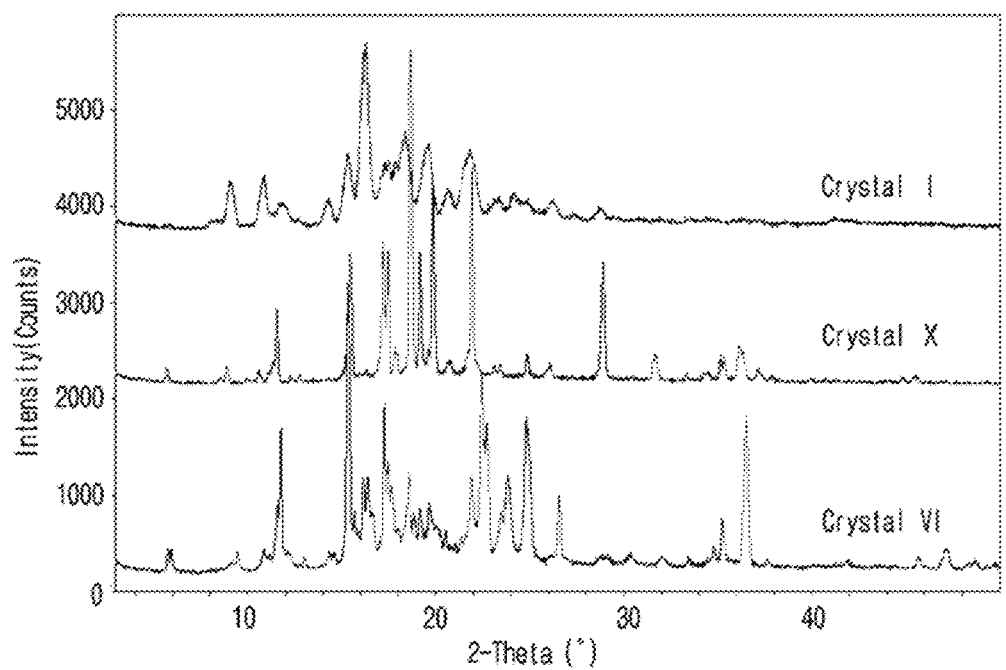
FIG. 13 is a graph showing the results of x-ray powder diffraction (XRPD) comparing the crystalline form X according to Example 10 with the crystalline forms I and VI.

The peaks having a relative intensity of 10% or more in XRPD spectrum of the crystalline form of FIG. 13 are shown in Table 12 below.

TABLE 12

| No. | 2θ (±0.2°) | d value (A) | I/I₀ (%) |
|---|---|---|---|
| 1 | 11.5 | 7.6 | 23.6 |
| 2 | 15.4 | 5.7 | 40.2 |
| 3 | 17.2 | 5.1 | 43.1 |
| 4 | 17.4 | 5.0 | 41.0 |
| 5 | 17.8 | 4.9 | 11.8 |
| 6 | 18.6 | 4.7 | 100.0 |
| 7 | 19.1 | 4.6 | 40.4 |
| 8 | 19.8 | 4.4 | 59.3 |
| 9 | 21.9 | 4.0 | 66.0 |
| 10 | 24.8 | 3.5 | 10.3 |
| 11 | 28.9 | 3.0 | 38.0 |
| 12 | 31.6 | 2.8 | 10.0 |
| 13 | 36.1 | 2.4 | 12.6 |

2θ: diffraction angle, dc distance between crystal faces, I/I₀ (%): relative intensity (I: intensity of each peak; I₀: intensity of highest peak)

When the relative intensity (I/I₀) of the peak was 10% or more, the peak had the diffraction angles of 11.5°, 15.4°, 17.2°, 17.4°, 17.8°, 18.6°, 19.1°, 19.8°, 21.9°, 24.8°, 28.9°, 31.6°, and 36.1° (2θ±0.2°). The crystalline form of the compound 1 having such a crystalline form is called the crystalline form X.

<Example 11> Scale up of Crystalline form V and Preparation of Crystalline form X I.

Figure 14:
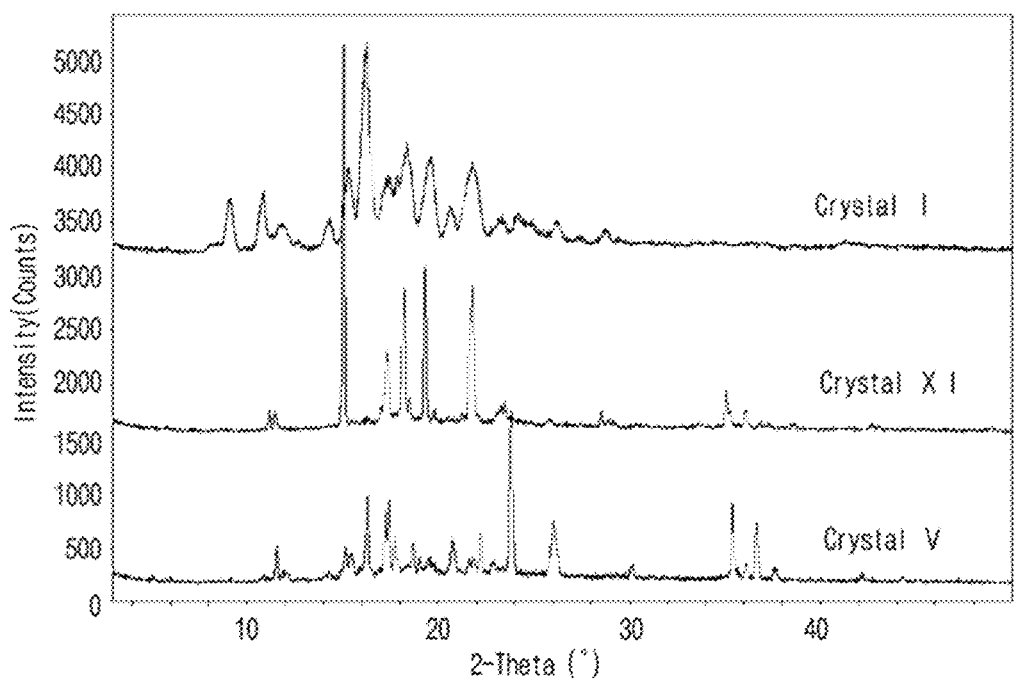
FIG. 14 is a graph showing the results of X-ray powder diffraction (XRPD) comparing the crystalline form X I according to Example II with the crystalline forms I and V.

The scale up of the crystalline form V prepared in Example 5 was performed as follows. About 100 mg of the compound 1 prepared in Preparative Example 1 was completely dissolved in n-butanol (1.6 mL) at 55° C. to prepare a saturated solution, followed by mixing continuously for 30 minutes. Then, the solution was rapidly cooled to low temperature in a −20° C. refrigerator, and stored for 3 days. After separating the prepared solid by centrifugation, it was dried in vacuo at 40° C. overnight. In order to analyze the characteristics of the crystalline form of the prepared solid, XRPD was performed according to the method described in <Experimental Methods>1. X-ray Powder Diffractometer (XRPD). The results are shown in Table 13 and FIG. 14. The peaks having a relative intensity (I/I₀) of 10% or more in XRPD spectrum of the crystalline form of FIG. 14 are shown in Table 13 below.

TABLE 13

| No. | 2θ (±0.2°) | d value (A) | I/I₀ (%) |
| --- | --- | --- | --- |
| 1 | 15.0 | 5.8 | 100.0 |
| 2 | 17.3 | 5.1 | 22.6 |
| 3 | 18.2 | 4.8 | 38.0 |
| 4 | 19.3 | 4.5 | 43.7 |
| 3 | 21.8 | 4.0 | 38.5 |
| 6 | 35.0 | 2.5 | 11.7 |

2θ: diffraction angle, d: distance between crystal faces, $I/I_0$ (%): relative intensity (I: intensity of each peak; $I_0$: intensity of highest peak)

When the relative intensity ($I/I_0$) of the peak was 10% or more, the peak had the diffraction angles of 15.0°, 17.3°, 18.2°, 19.3°, 21.8°, and 35.0° (2θ±0.2°). The crystalline form of the compound 1 having such a crystalline form is called the crystalline form X I.

<Experimental Example 1> Measurement of Purity According to Crystalline Form About 5 mg of each of the crystalline forms prepared in Preparative Example 1 and Examples 1 to 5 was weighed in a 10 mL volumetric flask and analyzed according to the following purity analysis method. 5 mg of each crystalline form in a stable state was dissolved in 10 mL acetonitrile, and 10 μL of the mixture was injected into HPLC. HPLC conditions were the same as in <Experimental Methods>6. High performance liquid chromatography (HPLC). The results are shown in Table 14.

TABLE 14

| Crystalline form | Purity (%) | Total related substance (%) |
| --- | --- | --- |
| Preparative Example 1 | 99.55 | 0.45 |
| Example 1 crystalline form I | 99.85 | 0.15 |
| Exampie 2 crystalline form II | 99.69 | 0.31 |
| Example 3 crystalline form III | 99.63 | 3.37 |
| Example 4 crystalline form IV | 99.55 | 0.45 |
| Example 5 crystalline form V | 99.74 | 0.26 |

<Experimental Example 2> Accelerated Stability Test

Since a significant change is judged and the expiration date is set based on a described stability test method in order to determine the storage method and period of use of drugs, etc., the stability test is one of the important factors in securing appropriate stability and commercialization of drugs and the like.

In order to confirm the stability of the novel crystalline form according to the present invention, the stability of the crystalline form I prepared in Example 1 was evaluated using a liquid chromatography method under the analysis conditions of <Experimental Methods>6. High performance liquid chromatography (HFLC). The results of the accelerated stability test from 1 month to 6 months in the conditions of 40±2° C. & 75±5 RH are shown in Table 15 below.

TABLE 15

| Crystalline form | Analysis condition | Storage time (month) | Purity (%) |
| --- | --- | --- | --- |
| Example 1 crystalline form I | 40 ± 2° C. & 75 ± 5% RH | Initial | 99.8 |
| | | 1 | 99.8 |
| | | 3 | 99.8 |
| | | 6 | 99.8 |

As a result, it was confirmed that the crystalline form I of Example 1 according to the present invention was stably maintained for up to 6 months without affecting the purity.

As mentioned above, the present invention has been described in detail through the preferred preparative examples, examples and experimental examples, but the scope of the present invention is not limited to the specific examples, and should be interpreted by the appended claims. In addition, those of ordinary skill in the art should understand that many modifications and variations are possible without departing from the scope of the present invention.

INDUSTRIAL APPLICABILITY

The present invention relates to a crystalline form of (E)-methyl 6-((3S,6S,9S,10R,13S,14S,17R)-3-(((5S,6R)-5-acetoxy-6-(acetoxymethyl)-5,6-dihydro-2Hpyran-2-yl)oxy)-10,13-dimethyl-2,3,4,7,8,9,10,11,12,13,14,15,16,17-tetradecahydro-1H-cyclopenta[a]phenanthrene-17-yl)hept-5-enoate and a vascular leakage blocker comprising the same. The novel crystalline form has high purity, excellent stability, excellent long-term storage and pharmaceutical stability, and can be used as a vascular leakage blocker, so it is very advantageous in producing high-quality drug substances.

The invention claimed is:

1. A crystalline form I of a compound represented by (E)-methyl 6-((3S,8S, 9S, 10R, 13S, 14S, 17R)-3-(((2S,5S, 6R)-5-acetoxy-6-(acetoxymethyl)-5,6-dihydro-2H-pyran-2-yl)oxy)-10,13-dimethyl-2, 3, 4, 7, 8, 9, 10, 11, 12, 13, 14, 15, 16,17-tetradecahydro-1H-cyclopenta[a]phenanthrene-17-yl)hept-5-enoate, wherein the crystalline form includes peaks at the following 2θ diffraction angles in the X-ray powder diffraction pattern:
  16.0°±0.2°, 19.5°±0.2°, 18.3°±0.2°, 15.1°±0.2°, 21.9°±0.2°.

2. The crystalline form I according to claim 1, wherein the crystalline form further includes peaks at the following 2θ diffraction angles:
  10.7°±0.2°, 8.9°±0.2°, 17.8°±0.2°, 21.3°±0.2°, 17.2°±0.2°.

3. The crystalline form I according to claim 2, wherein the crystalline form further includes peaks at the following 2θ diffraction angles:
  14.1°±0.2°, 20.5°±0.2°, 11.7°=0.2°.

4. The crystalline form I according to claim 3, wherein the crystalline form further includes peaks at the following 2θ diffraction angles:
  24.0°±0.2°, 24.6°±0.2°, 26.1°±0.2°.

5. A method of treating vascular leakage disease comprising administering to a subject in need thereof the crystalline form of claim 1.

* * * * *